US011046969B2

(12) United States Patent
Jia et al.

(10) Patent No.: US 11,046,969 B2
(45) Date of Patent: Jun. 29, 2021

(54) TRANSGENIC PLANT AND THE METHOD FOR PRODUCING THE SAME

(71) Applicant: EPIPLANTA BIOTECH LTD., Beijing (CN)

(72) Inventors: Guifang Jia, Beijing (CN); Chuan He, Beijing (CN)

(73) Assignee: EPIPLANTA BIOTECH LTD., Beijing (CN)

( * ) Notice: Subject to any disclaimer, the term of this patent is extended or adjusted under 35 U.S.C. 154(b) by 0 days.

(21) Appl. No.: 15/603,894

(22) Filed: May 24, 2017

(65) Prior Publication Data

US 2018/0340182 A1 Nov. 29, 2018

(51) Int. Cl.
*C12N 15/82* (2006.01)
*A01H 4/00* (2006.01)

(52) U.S. Cl.
CPC ......... *C12N 15/8261* (2013.01); *A01H 4/008* (2013.01); *C12Y 114/11033* (2013.01)

(58) Field of Classification Search
None
See application file for complete search history.

(56) References Cited

U.S. PATENT DOCUMENTS

| | | | |
|---|---|---|---|
| 4,959,317 A | 9/1990 | Sauer | |
| 5,352,605 A | 10/1994 | Fraley et al. | |
| 5,527,695 A | 6/1996 | Hodges et al. | |
| 5,550,318 A | 8/1996 | Adams et al. | |
| 5,633,435 A | 5/1997 | Barry et al. | |
| 5,780,708 A | 7/1998 | Lundquist et al. | |
| 6,118,047 A | 9/2000 | Anderson et al. | |
| 6,194,636 B1 | 2/2001 | McElroy et al. | |
| 6,232,526 B1 | 5/2001 | McElroy et al. | |
| RE39,247 E | 8/2006 | Barry et al. | |
| 7,619,146 B2 * | 11/2009 | Frankard .............. | C12N 9/0032 800/320.1 |
| 2016/0208243 A1 | 7/2016 | Zhang et al. | |
| 2018/0245128 A1 | 8/2018 | He et al. | |
| 2020/0370044 A1 | 11/2020 | Li et al. | |

FOREIGN PATENT DOCUMENTS

| | | | | |
|---|---|---|---|---|
| CN | 201310445072 | * | 4/2015 | ............. C12N 15/82 |
| CN | 104513831 B | | 12/2020 | |
| WO | 03/050287 A2 | | 6/2003 | |
| WO | 2004/058980 A2 | | 7/2004 | |
| WO | 2005/061702 A2 | | 7/2005 | |
| WO | WO-2017040477 A1 | | 3/2017 | |
| WO | WO-2019074960 A1 | | 4/2019 | |
| WO | WO-2020062264 A1 | | 4/2020 | |
| WO | WO-2020132536 A1 | | 6/2020 | |
| WO | WO-2021000889 A1 | | 1/2021 | |

OTHER PUBLICATIONS

NCBI Reference Sequence NP_001073901.1, Sep. 17, 2018 (Year: 2018).*
NCBI Reference Sequence NM_001080432.2, Sep. 17, 2018 (Year: 2018).*
Geneseq Accession No. AZZ05067, Oct. 25, 2012 (Year: 2012).*
Duan et al. English translation of CN 201310445072, Apr. 15, 2015 (Year: 2015).*
Dominissini D. et al., "Topology of the Human and Mouse m6 A RNA Methylomes Revealed by m6 A-Seq", Nature 485:201-208 (May 10, 2012).
Fu Y. et al., "FTO-Mediated Formation of N6-Hydroxymethyladenosine and N6-Formyladenosine in Mammalian RNA", Nature Communications 4:1798 (8 pages) (2013).
Jia G. et al., "N6-Methyladenosine in Nuclear RNA is a Major Substrate of the Obesity-Associated FTO", Nature Chemical Biology 7:885-887 (Dec. 2011).
Liu J. et al., "A METTL3-METTL14 Complex Mediates Mammalian Nuclear RNA N6-Adenosine Methylation", Nature Chemical Biology 10:93-95 (Feb. 2014).
Meyer K.D. et al., "Comprehensive Analysis of mRNA Methylation Reveals Enrichment in 3' UTRs and Near Stop Codons", Cell 149:1635-1646 (Jun. 22, 2012) and Supplemental Information.
Ping X-L et al., "Mammalian WTAP is a Regulatory Subunit of the RNA N6-Methyladenosine Methyltransferase", Cell Research 24:177-189 (2014).
Shen L. et al., "N6-Methyladenosine RNA Modification Regulates Shoot Stem Cell Fate in *Arabidopsis*", Developmental Cell 38:186-200 (Jul. 25, 2016).
Wang F-L et al., "*Escherichia coli* Acetyl-CoA Carboxylase (ACCase) accD Subunit Gene Expression Vector Construction and Genetic Transformation", Journal of Nuclear Agricultural Sciences 25(6):129-1134 (2011), together with an English-language abstract.
Zheng G. et al., "ALKBH5 is a Mammalian RNA Demethylase that Impacts RNA Metabolism and Mouse Fertility", Molecular Cell 49:18-29 (Jan. 10, 2013).
Zhong S. et al., "MTA is an *Arabidopsis* Messenger RNA Adenosine Methylase and Interacts With a Homolog of a Sex-Specific Splicing Factor", The Plant Cell 20:1278-1288 (May 2008).
Bodi Z. et al., "Adenosine methylation in *Arabidopsis* mRNA is associated with the 3' end and reduced levels cause developmental defects", Frontiers in Plant Science, (2012), vol. 3, 10 pages.

(Continued)

*Primary Examiner* — Cynthia E Collins
(74) *Attorney, Agent, or Firm* — Choate, Hall & Stewart LLP; Brenda Herschbach Jarrell; Xiaodong Li

(57) ABSTRACT

The present invention is directed to a transgenic plant and a method for producing the same. In particular, the present invention is directed to a transgenic plant or a plant cell in which a nucleic acid molecule encoding an $m^6A$ demethylase is introduced, wherein said $m^6A$ demethylase has the following two domains: i) N-terminal domain (NTD) having the function of AlkB oxidation demethylase; and ii) C-terminal domain (CTD). The present invention is also directed to a method for producing said plant, comprising introducing a nucleic acid molecule encoding an $m^6A$ demethylase into a regenerable plant cell, and regenerating a transgenic plant from the regenerable plant cell.

10 Claims, 1 Drawing Sheet
Specification includes a Sequence Listing.

(56) References Cited

OTHER PUBLICATIONS

Wang X. et al., "N6-methyladenosine-dependent regulation of messenger RNA stability", Nature, (2014), vol. 505, 22 pages.
Schwartz S. et al., "Perturbation of m6A Writers Reveals Two Distinct Classes of mRNA Methylation at Internal and 5' Sites", Cell Reports Resource, (2014), 8, pp. 284-296.
Luo G-Z. et al., "Unique features of the m6A methylome in *Arabidopsis thaliana*", Nature Communications, (2014), 8 pages.
Baurle I. et al., "The Timing of Developmental Transitions in Plants", Cell, (2006), 125, pp. 655-664.
Dai Z. et al., "Modulation of plant architecture by the miR156f-OsSPL7-OsGH3.8 pathway in rice", Journal of Experimental Botany, (2018), vol. 69, No. 21, pp. 5117-5130.
Ikeda A. et al., "slender Rice, a Constitutive Gibberellin Response Mutant, Is Caused by a Null Mutation of the SLR1 Gene, an Ortholog of the Height-Regulating Gene GAI/RGA/RHT/D8", The Plant Cell, (2001), vol. 13, pp. 999-1010.
Wang L. et al., "Coordinated regulation of vegetative and reproductive branching in rice", PNAS, (2015), vol. 112, No. 50, pp. 15504-15509.
Xue W. et al., "Natural variation in Ghd7 is an important regulator of heading date and yield potential in rice", Nature Genetics, (2008), vol. 40, No. 6, pp. 761-767.
Yue E. et al., "MiR529a modulates panicle architecture through regulating Squamosa Promoter Binding-Like genes in rice (*Oryza sativa*)", Plant Mol Biol, (2017), 94, pp. 469-480.
Zhang H. et al., "Delayed Heading Date1 interacts with OsHAP5C/D, delays flowering time and enhances yield in rice", Plant Biotechnology Journal, (2018), pp. 1-9.
Chen, B. et al., Development of cell-active N6-methyladenosine RNA demethylase FTO inhibitor, J Am Chem Soc., 134(43):17963-71 (2012).
Duan, H. et al., ALKBH10B is an RNA $N^6$-Methyladenosine Demethylase Affecting *Arabidopsis* Floral Transition, The Plant Cell, 29:2995-3011 (2017).

Huang, Y. et al., Meclofenamic acid selectively inhibits FTO demethylation of $m^6A$ over ALKBH5, Nucleic Acids Research, 43(1):373-384 (2015).
Jia, G. et al., Oxidative demethylation of 3-methylthymine and 3-methyluracil in single-stranded DNA and RNA by mouse and human FTO, FEBS Letters, 582:3313-3319 (2008).
Jia, G. et al., Reversible RNA adenosine methylation in biological regulation, Trends Genet., 29(2):108-15 (2013).
Liu, L. and Jia, G., Methylation modifications in eukaryotic messenger RNA, J Genet. Genomics, 41(1):21-33 (2014).
Song, H. et al., SFPQ is an FTO-Binding Protein that Facilitates the Demethylation Substrate Preference, Cell Chemical Biology, 27:283-291 (2020).
Wang, Y. and Jia, G., New Edges of RNA Adenosine Methylation Modifications, Genomics Proteomics Bioinformatics, 14(3):172-175 (2016).
Wang, Y. et al., Antibody-free enzyme-assisted chemical approach for detection of N6-methyladenosine, Nature Chemical Biology, 16:896-903 (2020).
Wei, L. et al., The $m^6A$ Reader ECT2 Controls Trichome Morphology by Affecting mRNA Stability in *Arabidopsis*, The Plant Cell, 30:968-985 (2018).
Xiao, Y. et al., An Elongation- and Ligation-Based qPCR Amplification Method for the Radiolabeling-Free Detection of Locus-Specific N6-Methyl-adenosine Modification, Angew. Chem. Int. Ed., 57:15995-16000 (2018).
Zhang, X. and Jia, G., RNA epigenetic modification: N6-methyladenosine, Yi Chuan, 38(4):275-88 (2016). English Abstract.
Zhang, X. et al., Structural insights into FTO's catalytic mechanism for the demethylation of multiple RNA substrates, PNAS, 116(8):2919-2924 (2019).
Zhao, X. et al., FTO-dependent demethylation of N6-methyladenosine regulates mRNA splicing and is required for adipogenesis, Cell Res., 24(12):1403-19 (2014).

* cited by examiner

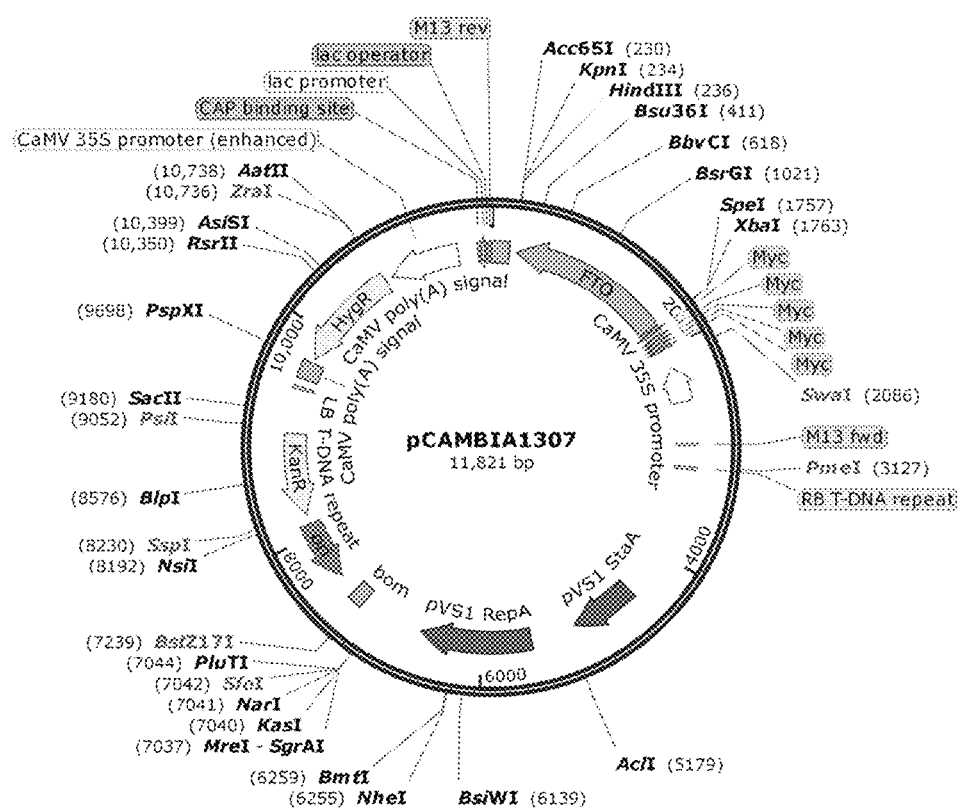

SEQUENCE LISTING

<160> NUMBER OF SEQ ID NOS: 20

<210> SEQ ID NO 1
<211> LENGTH: 505
<212> TYPE: PRT
<213> ORGANISM: Homo sapiens

<400> SEQUENCE: 1

Met Lys Arg Thr Pro Thr Ala Glu Glu Arg Glu Arg Glu Ala Lys Lys
1               5                   10                  15

Leu Arg Leu Leu Glu Glu Leu Glu Asp Thr Trp Leu Pro Tyr Leu Thr
            20                  25                  30

Pro Lys Asp Asp Glu Phe Tyr Gln Gln Trp Gln Leu Lys Tyr Pro Lys
        35                  40                  45

Leu Ile Leu Arg Glu Ala Ser Ser Val Ser Glu Glu Leu His Lys Glu
    50                  55                  60

Val Gln Glu Ala Phe Leu Thr Leu His Lys His Gly Cys Leu Phe Arg
65                  70                  75                  80

Asp Leu Val Arg Ile Gln Gly Lys Asp Leu Leu Thr Pro Val Ser Arg
                85                  90                  95

Ile Leu Ile Gly Asn Pro Gly Cys Thr Tyr Lys Tyr Leu Asn Thr Arg
            100                 105                 110

Leu Phe Thr Val Pro Trp Pro Val Lys Gly Ser Asn Ile Lys His Thr
        115                 120                 125

Glu Ala Glu Ile Ala Ala Ala Cys Glu Thr Phe Leu Lys Leu Asn Asp
    130                 135                 140

Tyr Leu Gln Ile Glu Thr Ile Gln Ala Leu Glu Glu Leu Ala Ala Lys
145                 150                 155                 160

Glu Lys Ala Asn Glu Asp Ala Val Pro Leu Cys Met Ser Ala Asp Phe
                165                 170                 175

Pro Arg Val Gly Met Gly Ser Ser Tyr Asn Gly Gln Asp Glu Val Asp
            180                 185                 190

Ile Lys Ser Arg Ala Ala Tyr Asn Val Thr Leu Leu Asn Phe Met Asp
        195                 200                 205

Pro Gln Lys Met Pro Tyr Leu Lys Glu Glu Pro Tyr Phe Gly Met Gly
    210                 215                 220

Lys Met Ala Val Ser Trp His His Asp Glu Asn Leu Val Asp Arg Ser
225                 230                 235                 240

Ala Val Ala Val Tyr Ser Tyr Ser Cys Glu Gly Pro Glu Glu Ser
            245                 250                 255

Glu Asp Asp Ser His Leu Glu Gly Arg Asp Pro Asp Ile Trp His Val
        260                 265                 270

Gly Phe Lys Ile Ser Trp Asp Ile Glu Thr Pro Gly Leu Ala Ile Pro
    275                 280                 285

Leu His Gln Gly Asp Cys Tyr Phe Met Leu Asp Asp Leu Asn Ala Thr
290                 295                 300

His Gln His Cys Val Leu Ala Gly Ser Gln Pro Arg Phe Ser Ser Thr
305                 310                 315                 320

His Arg Val Ala Glu Cys Ser Thr Gly Thr Leu Asp Tyr Ile Leu Gln
            325                 330                 335

Arg Cys Gln Leu Ala Leu Gln Asn Val Cys Asp Asp Val Asp Asn Asp
        340                 345                 350

Asp Val Ser Leu Lys Ser Phe Glu Pro Ala Val Leu Lys Gln Gly Glu
    355                 360                 365

Glu Ile His Asn Glu Val Glu Phe Glu Trp Leu Arg Gln Phe Trp Phe
370                 375                 380

Gln Gly Asn Arg Tyr Arg Lys Cys Thr Asp Trp Trp Cys Gln Pro Met
385                 390                 395                 400

Ala Gln Leu Glu Ala Leu Trp Lys Lys Met Glu Gly Val Thr Asn Ala
            405                 410                 415

Val Leu His Glu Val Lys Arg Glu Gly Leu Pro Val Glu Gln Arg Asn
        420                 425                 430

Glu Ile Leu Thr Ala Ile Leu Ala Ser Leu Thr Ala Arg Gln Asn Leu
    435                 440                 445

Arg Arg Glu Trp His Ala Arg Cys Gln Ser Arg Ile Ala Arg Thr Leu
450                 455                 460

Pro Ala Asp Gln Lys Pro Glu Cys Arg Pro Tyr Trp Glu Lys Asp Asp
465                 470                 475                 480

Ala Ser Met Pro Leu Pro Phe Asp Leu Thr Asp Ile Val Ser Glu Leu
            485                 490                 495

Arg Gly Gln Leu Leu Glu Ala Lys Pro
        500                 505

<210> SEQ ID NO 2
<211> LENGTH: 505
<212> TYPE: PRT
<213> ORGANISM: Sus scrofa

<400> SEQUENCE: 2

Met Lys Arg Thr Pro Thr Ala Glu Glu Arg Glu Arg Gly Ala Lys Lys
1               5                   10                  15

Leu Arg Leu Leu Glu Glu Leu Glu Asp Thr Trp Leu Pro Tyr Leu Thr
            20                  25                  30

Pro Lys Asp Asp Glu Phe Tyr Gln Gln Trp Gln Leu Lys Tyr Pro Lys
        35                  40                  45

Leu Ile Leu Arg Glu Ala Gly Ser Val Pro Glu Gly Leu His Lys Glu
    50                  55                  60

Val Gln Glu Ala Phe Leu Ala Leu His Lys His Gly Cys Leu Phe Arg
65                  70                  75                  80

Asp Leu Val Arg Ile Gln Gly Lys Asp Leu Leu Thr Pro Val Ser Arg
            85                  90                  95

Leu Leu Ile Gly Asn Pro Gly Cys Thr Tyr Lys Tyr Leu Asn Thr Arg

```
            100                 105                 110
Leu Phe Thr Val Pro Trp Pro Val Lys Gly Ser Asp Ala Lys Tyr Asn
        115                 120                 125

Glu Ala Glu Ile Gly Ala Ala Cys Gln Thr Phe Leu Lys Leu Asn Asp
        130                 135                 140

Tyr Leu Gln Ile Glu Thr Ile Gln Ala Leu Glu Leu Ala Ala Lys
145                 150                 155                 160

Glu Lys Ala Asn Ile Asp Thr Val Pro Ala Cys Ile Gly Pro Asp Phe
                165                 170                 175

Pro Arg Val Gly Met Gly Ser Ser Phe Asp Gly His Asp Glu Val Asp
            180                 185                 190

Arg Lys Ser Arg Ala Ala Tyr Asn Leu Thr Leu Leu Ser Phe Met Asp
        195                 200                 205

Pro Gln Lys Met Pro Tyr Leu Lys Glu Pro Tyr Phe Gly Met Gly
        210                 215                 220

Lys Met Ala Val Ser Trp His His Asp Glu Asn Leu Val Asp Arg Ser
225                 230                 235                 240

Ala Val Ala Val Tyr Asn Tyr Ser Cys Glu Gly Pro Glu Glu Glu Ser
                245                 250                 255

Glu Asp Asp Pro Gln Leu Glu Gly Arg Asn Pro Asp Val Trp His Val
            260                 265                 270

Gly Phe Lys Ile Ser Trp Asp Ile Glu Thr Pro Gly Leu Ala Ile Pro
        275                 280                 285

Leu His Gln Gly Asp Cys Tyr Phe Met Leu Asp Asp Leu Asn Ala Thr
    290                 295                 300

His Gln His Cys Val Leu Ala Gly Leu Pro Pro Arg Phe Ser Ser Thr
305                 310                 315                 320

His Arg Val Ala Glu Cys Ser Thr Gly Ala Leu Asp Tyr Ile Leu Gln
                325                 330                 335

Arg Cys Gln Leu Ala Leu Gln Asn Val Arg Asp Glu Ala Asp Ser Gly
            340                 345                 350

Glu Val Ser Leu Lys Ser Leu Glu Pro Ala Val Leu Lys Gln Gly Glu
        355                 360                 365

Glu Ile His Asn Glu Val Glu Phe Glu Trp Leu Arg Gln Phe Trp Phe
    370                 375                 380

Gln Gly Asn Arg Tyr Lys Lys Cys Thr Asp Trp Trp Cys Gln Pro Met
385                 390                 395                 400

Thr Gln Leu Glu Glu Leu Trp Lys Lys Met Glu Gly Ala Thr His Ala
                405                 410                 415

Val Leu Arg Glu Val Arg Arg Glu Gly Ala Pro Val Glu Gln Ser Ser
            420                 425                 430

Asp Ile Leu Thr Ala Ile Leu Ala Val Leu Thr Thr Arg Gln Asn Leu
        435                 440                 445

Arg Arg Glu Trp His Ala Arg Cys Gln Ser Arg Ile Ala Arg Thr Leu
    450                 455                 460

Pro Val Asp Gln Lys Pro Glu Cys Arg Pro Tyr Trp Glu Lys Asp Asp
465                 470                 475                 480

Pro Ser Met Pro Leu Pro Phe Asp Leu Thr Asp Thr Val Ala Glu Leu
                485                 490                 495

Arg Gly Leu Leu Leu Glu Ala Lys Pro
            500                 505

<210> SEQ ID NO 3
```

<211> LENGTH: 505
<212> TYPE: PRT
<213> ORGANISM: Bos taurus

<400> SEQUENCE: 3

```
Met Lys Arg Thr Pro Thr Ala Glu Glu Arg Glu Arg Glu Ala Lys Lys
1               5                   10                  15

Leu Arg Leu Leu Glu Glu Leu Glu Asp Thr Trp Leu Pro Tyr Leu Thr
            20                  25                  30

Pro Lys Asp Asp Glu Phe Tyr Gln Gln Trp Gln Leu Lys Tyr Pro Lys
        35                  40                  45

Leu Ile Leu Arg Glu Ala Ala Ser Val Pro Glu Leu Leu His Lys Glu
50                  55                  60

Val Gln Gln Ala Phe Leu Thr Leu His Lys His Gly Cys Leu Phe Arg
65                  70                  75                  80

Asp Leu Val Arg Ile Gln Gly Lys Asp Leu Leu Thr Pro Val Ser Arg
                85                  90                  95

Ile Leu Ile Gly Asn Pro Gly Cys Thr Tyr Lys Tyr Leu Asn Thr Arg
            100                 105                 110

Leu Phe Thr Val Pro Trp Pro Val Lys Gly Ser Asp Ala Lys Tyr Asn
        115                 120                 125

Glu Ala Glu Ile Ala Ala Ala Cys Gln Thr Phe Leu Lys Leu Asn Ser
130                 135                 140

Tyr Leu Gln Val Glu Thr Ile Gln Ala Leu Glu Leu Ala Ala Lys
145                 150                 155                 160

Glu Lys Ala Asn Ile Asp Ala Val Pro Val Cys Ile Gly Pro Asp Phe
                165                 170                 175

Pro Arg Val Gly Met Gly Ser Ser Phe Asp Gly His Asp Glu Ile Asp
            180                 185                 190

Met Lys Asn Arg Ala Ala Tyr Asn Val Thr Leu Leu Asn Phe Met Asp
        195                 200                 205

Pro Gln Lys Met Pro Tyr Leu Lys Glu Glu Pro Tyr Phe Gly Met Gly
210                 215                 220

Lys Met Ala Val Ser Trp His His Asp Glu Asn Leu Val Asp Arg Ser
225                 230                 235                 240

Ala Val Ala Val Tyr Ser Tyr Ser Cys Glu Gly Pro Glu Glu Glu Ser
                245                 250                 255

Glu Asp Asp Pro Gln Leu Glu Gly Arg Asp Pro Asp Ile Trp His Val
            260                 265                 270

Gly Phe Lys Ile Ser Trp Asp Ile Glu Thr Pro Gly Leu Ala Ile Pro
        275                 280                 285

Leu His Gln Gly Asp Cys Tyr Phe Met Leu Asp Asp Leu Asn Ala Thr
290                 295                 300

His Gln His Cys Val Leu Ala Gly Leu Pro Pro Arg Phe Ser Ser Thr
305                 310                 315                 320

His Arg Val Ala Glu Cys Ser Thr Gly Thr Leu Glu Tyr Ile Leu Gln
                325                 330                 335

Arg Cys Gln Val Ala Leu Gln Asn Val Arg Glu Glu Ala Asp Asn Gly
            340                 345                 350

Glu Ile Ser Leu Lys Ser Leu Glu Ser Val Val Leu Lys Gln Gly Glu
        355                 360                 365

Glu Ile His Asn Glu Val Glu Phe Glu Trp Leu Arg Gln Phe Trp Phe
370                 375                 380

Gln Gly Ser Arg Tyr Lys Lys Cys Thr Asp Trp Trp Cys Gln Pro Met
```

```
                385                 390                 395                 400
Ser Gln Leu Glu Glu Met Trp Arg Lys Met Glu Trp Leu Thr Ser Ala
                    405                 410                 415

Val Leu Arg Glu Val Arg Arg Glu Gly Val Pro Met Glu Gln Lys Asn
                    420                 425                 430

Glu Met Leu Thr Ser Ile Leu Ala Ser Ile Thr Thr Arg Gln Asn Leu
                    435                 440                 445

Arg Arg Glu Trp His Ala Arg Cys Gln Ser Arg Ile Ala Arg Thr Leu
                    450                 455                 460

Pro Ala Asp Gln Lys Pro Glu Cys Arg Pro Tyr Trp Glu Lys Gly Asp
465                 470                 475                 480

Pro Ser Met Pro Leu Pro Phe Asp Leu Thr Glu Ile Val Ser Glu Leu
                    485                 490                 495

Arg Gly Leu Leu Leu Glu Thr Arg Pro
                    500                 505

<210> SEQ ID NO 4
<211> LENGTH: 419
<212> TYPE: PRT
<213> ORGANISM: Ostreococcus lucimarinus

<400> SEQUENCE: 4

Met Ser Pro Ser Ser Val Leu Glu Pro Glu Asp Gly Glu Pro Phe
1               5                   10                  15

Ala Arg Val His Arg Ala His Tyr Arg Gly Phe Val Val Asp Ala Pro
                20                  25                  30

Ser Val Leu Pro Ala Ser Leu His Asp Asp Val Glu Arg Ala Phe Asp
                35                  40                  45

Asp Met Arg Ser Arg Gly Glu Phe Thr His Asp Val Val Ser Ala Gly
            50                  55                  60

Asn Lys Val Ser Thr Thr Tyr Val Arg Arg Cys Leu Leu Gly Glu Asp
65                  70                  75                  80

Gly Met Thr Tyr His Tyr Gln Lys Leu Arg Leu Phe Ala Gln Pro Trp
                    85                  90                  95

Arg Gly Arg Glu Ala Tyr Glu Val Val Arg Arg Leu Asn Glu Thr Leu
                100                 105                 110

Thr Arg Ser Ala Arg Glu Arg Cys Glu Lys Leu Gly Gly Ala Phe Ala
                115                 120                 125

Glu Ser Glu Cys Glu Tyr Asn Val Thr Leu Ile Asn Tyr Met Glu Thr
130                 135                 140

Glu Gly Glu Ser Glu Ile Glu Leu Arg Asn Glu Glu Lys Phe Asp Leu
145                 150                 155                 160

Gly Thr Thr Ser Val Ser Trp His Ser Asp Ser Ser Leu Arg Glu Asn
                165                 170                 175

Ser Thr Val Ala Val Tyr His Thr Tyr Glu Ala Pro Glu Arg Lys Asp
                180                 185                 190

Trp Arg Val Ala Leu Arg Ala Leu Asn Ala Glu Cys Glu Val Leu Cys
                195                 200                 205

Val Pro Leu Glu Asp Lys Ala Thr Tyr Tyr Met Cys Gly Glu Phe Asn
                210                 215                 220

Ala Thr His His Ala Val Leu Thr Gly Ser Ser Ala Arg Tyr Ser
225                 230                 235                 240

Ser Thr His Arg Val Ala Val Ala Lys Asp Thr Phe Gln Tyr Ile
                245                 250                 255
```

Lys Arg Arg Cys Ile Asp Ala Leu Ala Ile Val Pro Asp Leu Glu Arg
                260                 265                 270

Glu Asn Lys Pro Leu Asp Ala Lys Gln Ile Gln Phe Leu Ala Asp Val
            275                 280                 285

His Arg Glu Val Glu Phe Gln Trp Ile Arg Met Phe His Leu Gln Gly
        290                 295                 300

Glu Ala His Ala Ala Trp His Asp Thr Tyr Trp Thr Arg Lys Ile Ala
305                 310                 315                 320

Glu Leu Thr Glu Ala Trp Asp Arg Met Glu Ala Cys Phe Arg Val Ile
                325                 330                 335

Leu Ser Lys Leu Lys Arg Ser Ser Arg Ser Pro Glu Ser Pro Pro Arg
            340                 345                 350

Ala Tyr Ala Met Leu Leu Tyr Ala Leu Lys Thr Val Lys Glu Leu Arg
        355                 360                 365

Asp Glu Tyr Thr Lys Arg Thr Lys Ala Ser Ala Tyr Ala Ser Leu Pro
370                 375                 380

Pro Ser Gln Arg Pro Val Asp Leu Pro Ala Tyr Asp Asn Thr Ser Pro
385                 390                 395                 400

Leu Pro Phe Glu Leu Lys Pro Val Ile Tyr Phe Leu Glu Glu Glu Gln
                405                 410                 415

Asn Lys Val

<210> SEQ ID NO 5
<211> LENGTH: 1518
<212> TYPE: DNA
<213> ORGANISM: Homo sapiens

<400> SEQUENCE: 5

```
atgaagcgca ccccgactgc cgaggaacga gagcgcgaag ctaagaaact gaggcttctt      60
gaagagcttg aagacacttg gctcccttat ctgaccccca agatgatga attctatcag     120
cagtggcagc tgaaatatcc taaactaatt ctccgagaag ccagcagtgt atctgaggag     180
ctccataaag aggttcaaga agcctttctc acactgcaca agcatggctg cttatttcgg     240
gacctggtta ggatccaagg caaagatctg ctcactccgg tatctcgcat cctcattggt     300
aatccaggct gcacctacaa gtacctgaac accaggctct ttacggtccc ctggccagtg     360
aaagggtcta atataaaaca caccgaggct gaaatagccg ctgcttgtga gaccttcctc     420
aagctcaatg actacctgca gatagaaacc atccaggctt ggaagaact tgctgccaaa     480
gagaaggcta atgaggatgc tgtgccattg tgtatgtctg cagatttccc cagggttggg     540
atgggttcat cctacaacgg acaagatgaa gtggacatta gagcagagc agcatacaac     600
gtaactttgc tgaatttcat ggatcctcag aaaatgccat acctgaaaga ggaaccttat     660
tttggcatgg ggaaatggc agtgagctgg catcatgatg aaaatctggt ggacaggtca     720
gcggtggcag tgtacagtta tagctgtgaa ggccctgaag aggaaagtga ggatgactct     780
catctcgaag gcagggatcc tgatatttgg catgttggtt taagatctc atgggacata     840
gagacacctg gtttggcgat acccttcac caaggagact gctatttcat gcttgatgat     900
ctcaatgcca cccaccaaca ctgtgttttg gccggttcac aacctcggtt tagttccacc     960
caccgagtgg cagagtgctc aacaggaacc ttggattata ttttacaacg ctgtcagttg    1020
gctctgcaga atgtctgtga cgatgtggac aatgatgatg tctctttgaa atcctttgag    1080
cctgcagttt tgaacaagg agaagaaatt cataatgagg tcgagtttga gtggctgagg    1140
cagttttggt ttcaaggcaa tcgatacaga aagtgcactg actggtggtg tcaacccatg    1200
```

```
gctcaactgg aagcactgtg gaagaagatg gagggtgtga caaatgctgt gcttcatgaa   1260
gttaaaagag aggggctccc cgtggaacaa aggaatgaaa tcttgactgc catccttgcc   1320
tcgctcactg cacgccagaa cctgaggaga gaatggcatg ccaggtgcca gtcacgaatt   1380
gcccgaacat tacctgctga tcagaagcca gaatgtcggc catactggga aaaggatgat   1440
gcttcgatgc ctctgccgtt tgacctcaca gacatcgttt cagaactcag aggtcagctt   1500
ctggaagcaa aaccctag                                                 1518
```

<210> SEQ ID NO 6
<211> LENGTH: 1515
<212> TYPE: DNA
<213> ORGANISM: Homo sapiens

<400> SEQUENCE: 6

```
atgaagcgca cccctactgc tgaggagaga gagagggagg ccaagaagct cagactcctg     60
gaggagctgg aggatacctg gctcccttac ctgactccca aggatgacga gttctaccag    120
caatggcagc tcaagtaccc caagctcatt ctgagggagg cttcctctgt ttccgaggag    180
ctgcacaagg aggtgcaaga ggccttcctt actttgcaca gcatggatg ccttttcaga    240 gatttggtta ggatccaggg caaggacctt ttgaccccg tgagcaggat tctcatcgga    300
aacccaggtt gcacttacaa gtacctcaat actcgcctgt tcacagtgcc atggcctgtt    360
aagggctcaa acattaagca tactgaggct gagatcgccg ctgcctgcga cattcctc     420 aagctgaatg attacctcca gattgagaca atccaagctc ttgaggagtt ggctgccaag    480
gagaaggcta acgaggatgc cgttccactg tgcatgtccg ccgacttccc tagagtgggc    540
atgggaagct catacaatgg ccaagatgag gttgacatta agtctagggc tgcctacaac    600
gtgaccctcc tgaatttcat ggacccacag aagatgcctt accttaagga ggagccatac    660
ttcggtatgg gcaagatggc tgtttcctgg caccatgatg agaacttggt ggacaggtct    720
gctgtggccg tttacagcta tcatgcgag ggacctgagg aggagagcga ggatgactca    780
cacctggagg gtcgcgatcc cgacatttgg catgttggct tcaagatttc ttgggatatc    840
gagacccctg gccttgccat ccccttgcac cagggagact gctacttcat gctcgatgac    900
ctgaatgcta cacaccagca ttgcgttctt gccggttccc aaccacgctt ctcctctacc    960
catagagtgg ctgagtgctc tacaggcacc ctcgattaca ttctgcagag atgccaactt   1020
gccttgcaaa acgtgtgcga tgacgttgac aatgatgacg tttcccttaa gtctttcgag   1080
cctgctgtgt tgaagcaggg agaggagatc cacaacgagg ttgagttcga gtggctgcgc   1140
cagttctggt tccaaggtaa tcgctacaga aagtgcactg attggtggtg ccagccaatg   1200
gctcaacttg aggccttgtg gaagaagatg gagggcgtga caaacgccgt tctccacgag   1260
gtgaagaggg agggactgcc tgtggagcaa cgcaacgaga ttcttacagc tatcctcgcc   1320
agcctgaccg ctagacagaa tttgaggcgc gagtggcatg ccaggtgcca atcaaggatt   1380
gctcgcaccc ttccagctga ccagaagcca gagtgcaggc catactggga aaggatgac   1440 gctagcatgc cccttccatt cgatttgact gacatcgtgt cagagttgag aggccagctt   1500
ttggaggcca agcca                                                    1515
```

<210> SEQ ID NO 7
<211> LENGTH: 1518
<212> TYPE: DNA
<213> ORGANISM: Sus scrofa

<400> SEQUENCE: 7

```
atgaagcgaa cccccaaccgc cgaggaacga gagcgcggag ctaagaaact gaggcttctt      60
gaagagctgg aagacacttg gcttccttat ctgacccccca aagatgatga attctatcag    120
cagtggcagc tgaaatcccc taagctaatt ctccgagaag caggcagcgt ccctgaggga    180
ctccacaaag aggttcaaga agccttcctc gcactgcaca agcatggctg cttatttcgg    240
gacctggtca ggatccaagg caaagatttg ctcacgccag tatctcgcct cctcattggt    300
aaccccggct gcacctacaa gtacctgaac accaggctct tcacggtccc ctggccagtg    360
aagggctctg atgcaaagta caatgaggcc gagataggcg ccgcctgcca gaccttcctc    420
aagctcaacg actacctgca gattgagacc atccaggcgc tggaggaact cgctgccaag    480
gagaaagcca atatcgacac cgtgccggcg tgtataggtc cagatttccc cagggtcggc    540
atggggtcat cctttgacgg ccatgacgag gtggacagga gagcagagc cgcctacaac    600
ctaactttgt tgagcttcat ggatcccccag aaaatgccgt acctgaaaga ggagccctac    660
tttggcatgg ggaagatggc tgtgagctgg catcacgatg aaaatctggt ggacaggtca    720
gcggtggcag tgtacaatta tagctgtgaa ggccctgaag aggaaagcga ggatgatccc    780
cagctcgaag gcagaaatcc cgatgtgtgg catgttggct ttaagatctc atgggacata    840
gagacccctg gtttggcgat acccccttcac caaggagact gctactttat gctggatgat    900
ctcaatgcca cccaccaaca ctgtgttttg gctggtttac caccccggtt tagttccacc    960
caccgagtgg ccgagtgctc gacgggagcc ttggattaca tcttacagcg ctgccagttg   1020
gccctgcaga atgtccgtga tgaggcggac agtggtgaag tctctttgaa atccttggag   1080
cctgcggttt tgaaacaagg agaagaaatc cacaacgagg tcgagtttga gtggctgaga   1140
cagttttggt ttcaaggcaa tcgatacaaa aagtgcaccg attggtggtg tcaacccatg   1200
actcagctgg aagagctttg gaagaagatg gaaggtgcga cccatgctgt gcttcgtgaa   1260
gttagaagag aggggggccccc tgtggaacag agcagtgaca tcctgactgc catcctagcc   1320
gtgctcacca ctcgccagaa cctgaggagg agtggcatg ccaggtgcca gtcccgaatt   1380
gcccgaactc tgcctgtgga ccagaagcca gaatgccggc cgtattggga aaaggatgat   1440
ccctccatgc ctctgccgtt tgatctcaca gacactgtgg ctgaactcag aggtctgctt   1500
ctggaagcca aaccctag                                                  1518
```

<210> SEQ ID NO 8
<211> LENGTH: 1515
<212> TYPE: DNA
<213> ORGANISM: Sus scrofa

<400> SEQUENCE: 8

```
atgaagagaa caccaaccgc tgaggagagg gagagaggag ctaagaagtt gaggctcctg      60
gaggagctgg aggacacatg gttgccctac ctcacccccaa aggatgacga gttctaccag    120
caatggcaat tgaagtaccc caagttgatt ctcagggagg ctggatctgt gccagaggga    180
ctgcacaagg aggttcaaga ggccttcctg gctcttcaca agcatggctg cctgttccgc    240
gaccttgtta gaattcaggg aaaggatctt ttgactccag tgtctcgcct cctgatcgga    300
aaccctggtt gcacatacaa gtacttgaat accagactct tcactgtgcc ctggccagtt    360
aagggtagcg acgccaagta caacgaggct gagatcggcg ccgcttgcca gacattcttg    420
aagctcaatg attacctgca gattgagacc atccaagctc tggaggagct tgccgctaag    480
gagaaggcca acattgacac tgttcctgct tgcatcggcc cagatttccc tagggtgggc    540
```

-continued

```
atgggatcct ctttcgatgg acatgacgag gttgatagga agtcacgcgc cgcttacaat    600
ttgacacttt tgtccttcat ggatcctcaa aagatgccct acctcaagga ggagccctac    660
ttcggtatgg gcaagatggc cgtgtcatgg caccatgacg agaaccttgt tgatagatcc    720
gccgtggctg tttacaatta ctcttgcgag ggccctgagg aggagagcga ggatgaccct    780
cagctggagg gaaggaaccc cgacgtgtgg cacgttggtt tcaagattag ctgggatatc    840
gagacccccg gtctggctat tccacttcat caaggcgact gctacttcat gttgatgac     900 ctcaatgcca ctcaccagca ttgcgttctg gctggacttc cacctaggtt cagctcaact    960
caccgcgtgg ccgagtgctc tacaggtgct ttggattaca ttctccagcg ctgccaactg   1020
gcccttcaaa acgtgagaga cgaggctgat agcggcgagg ttagcttgaa gtccctggag   1080
ccagctgtgc tgaagcaggg agaggagatc ataacgagg tggagttcga gtggcttaga   1140
cagttctggt tccaaggcaa taggtacaag aagtgcaccg actggtggtg ccagccaatg   1200
actcaactgg aggagctttg gaagaagatg gaggagccca cacacgctgt gctcagggag   1260
gttaggcgcg agggtgctcc tgttgagcag tcctctgaca ttctgaccgc catcttggct   1320
gtgctcacca ctaggcagaa tcttagaagg gagtggcatg cccgctgcca atcaagaatc   1380
gctaggaccc tgcctgttga tcagaagcca gagtgcaggc cttactggga aaggatgac    1440 ccctccatgc ctctgccctt cgaccttact gatacagtgg ccgagcttcg cggactcctg   1500
cttgaggcta agcct                                                    1515
```

<210> SEQ ID NO 9
<211> LENGTH: 1518
<212> TYPE: DNA
<213> ORGANISM: Bos taurus

<400> SEQUENCE: 9

```
atgaagcgga ccccgacggc cgaggaacga gagcgcgaag ctaagaaact gaggcttctt     60
gaagagcttg aagacacgtg gcttccctac ctgaccccca aagacgatga attctatcag    120
cagtggcaac tgaaatatcc taaactaatt ctccgagaag ctgccagcgt gcctgagttg    180
ctccataaag aggttcaaca agccttctc acgctgcaca gcacggctg tttatttcgg     240 gatctggtga ggatccaggg caaagacttg ctcactccag tctctcgcat cctcatcggt    300
aaccccggct gcacctacaa gtacctgaac accaggctct tcacggtacc ctggcccgtg    360
aaaggctctg atgcaaagta caatgaggcc gaaatagctg ccgcctgtca acgttcctc    420 aagctcaaca gctacctgca ggtagagacc atccaggctt ggaagagct tgctgccaag    480 gagaaagcca acatcgatgc cgtgccagtg tgcataggtc cagatttccc caggggttggc   540 atggggtcct cctttgacgg gcacgatgag attgacatga agaaccgagc agcgtacaac    600
gtcactttgt tgaatttcat ggatccccag aagatgccat acctgaaaga ggaaccgtat    660
tttggcatgg ggaaaatggc cgtgagctgg catcatgatg aaaatctggt ggacaggtca   720
gcggtggcag tgtacagtta tagctgtgaa ggccctgaag aggaaagtga ggacgaccct    780
cagcttgaag gcagagatcc tgatatttgg cacgttggtt ttaagatctc gtgggacata    840
gagacacctg gtttggcgat accccttcac caaggagact gctattttat gcttgatgat    900
ctcaatgcca cccaccaaca ctgtgttttg gctggtttac cacctcggtt tagttccacc    960
caccgagtgg cagagtgctc aacagggacc ttggagtaca tcttacagcg ctgccaggtg   1020
gccctgcaga atgtccgcga ggaggcagac aacggtgaaa tctctctgaa atccttggag   1080
```

| | | |
|---|---|---|
| tcagtggttt tgaaacaagg agaagaaatc cacaacgagg tcgagtttga atggctgaga | 1140 | |
| cagttttggt ttcaaggcag tcgatacaaa aagtgcactg actggtggtg tcagcccatg | 1200 | |
| agtcagctgg aagagatgtg gagaaagatg gagtggttga caagcgctgt gcttcgcgaa | 1260 | |
| gttagaagag aggggtccc catgaacaa aagaatgaga tgttgacatc catcctcgcc | 1320 | |
| tcgatcacca ctcgccagaa cctgaggaga gaatggcatg ccaggtgcca gtctcgaatt | 1380 | |
| gcccgaactt tacccgctga tcagaagcca gaatgccggc cgtactggga aaagggtgat | 1440 | |
| ccttcgatgc ctctgccatt tgatctcaca gagatcgttt ctgaactcag aggtctgctt | 1500 | |
| ctggaaacca ggccctag | 1518 | |

```
<210> SEQ ID NO 10
<211> LENGTH: 1515
<212> TYPE: DNA
<213> ORGANISM: Bos taurus

<400> SEQUENCE: 10
```

| | | |
|---|---|---|
| atgaagcgca caccaaccgc tgaggagcgc gagagagagg ccaagaagct gagactcctg | 60 | |
| gaggagcttg aggacacatg gctgccctac cttaccccaa aggatgacga gttctaccag | 120 | |
| caatggcaac ttaagtaccc caagttgatt ctcaggggag ccgctagcgt gccagagctt | 180 | |
| ttgcacaagg aggttcagca ggccttcctc acccttcaca agcatggatg cttgttcaga | 240 | |
| gacctcgtga ggatccaggg caaggatctc ctgaccccag tttcaaggat tctgatcgga | 300 | |
| aatcctggtt gcacttacaa gtacctgaac acccgccttt tcactgtgcc ctggccagtt | 360 | |
| aagggaagcg acgctaagta caatgaggcc gagattgccg ctgcctgcca gactttcttg | 420 | |
| aagctcaact cataccttca ggtggagaca atccaggccc tggaggagct cgctgccaag | 480 | |
| gagaaggcta atattgacgc cgtgcctgtt tgcatcggcc cagatttccc tagagtgggc | 540 | |
| atgggatcct ctttcgatgg acatgacgag attgatatga gaacagggc tgcctacaat | 600 | |
| gttactcttt tgaacttcat ggatcctcaa aagatgccct acttgaagga ggagccctac | 660 | |
| ttcggtatgg gcaagatggc cgtgtcatgg caccatgacg agaatctcgt tgatcgctcc | 720 | |
| gctgtggccg tttactccta ctcttgcgag ggccctgagg aggagtccga ggatgaccct | 780 | |
| cagctggagg gtagagatcc cgacatttgg cacgttggct tcaagatttc ttgggacatc | 840 | |
| gagacacccg gcttggctat cccactccat caaggagatt gctacttcat gctggatgac | 900 | |
| cttaacgcta ctcaccagca ttgcgtgttg gccggactcc cacctcgctt cagctcaaca | 960 | |
| cacagagttg ccgagtgctc cactggtaca ctggagtaca tccttcagcg ctgccaagtg | 1020 | |
| gctttgcaaa atgttagaga ggaggccgac aacggtgaaa ttagcctgaa gtcacttgag | 1080 | |
| tccgtggttt tgaagcaggg cgaggagatc cataacgagg tggagttcga gtggctcaga | 1140 | |
| cagttctggt tccaaggttc aaggtacaag aagtgcaccg attggtggtg ccagccaatg | 1200 | |
| tcccaactgg aggagatgtg gagaaagatg gagtggttga cttctgctgt gctcagggag | 1260 | |
| gttaggaggg agggcgttcc tatggagcag aagaatgaga tgttgacatc tattctcgct | 1320 | |
| agcatcacca ctaggcagaa cctgagaagg gagtggcacg cccgctgcca atctaggatt | 1380 | |
| gctcgcaccc ttcctgccga tcagaagcca gagtgccgcc ttactggga aagggcgac | 1440 | |
| ccctctatgc ctctgccctt cgatcttaca gagatcgtga gcgagctgag gggactcctg | 1500 | |
| cttgagaccc gccca | 1515 | |

```
<210> SEQ ID NO 11
<211> LENGTH: 1260
```

<212> TYPE: DNA
<213> ORGANISM: Ostreococcus lucimarinus

<400> SEQUENCE: 11

```
atgtcgccgt catcctccgt gctcgaaccc gaggacggcg aaccgttcgc gcgcgtccat    60
cgagcgcact accgcggttt cgtcgtggac gcgccctcgg tgcttcccgc gtcgcttcac   120
gacgacgtcg aacgcgcgtt cgacgacatg cgcagccgag gcgaattcac gcacgacgtc   180
gtttccgccg gaaataaagt gtccacgacg tacgtgcggc gctgcctgct cggtgaggac   240
ggaatgacgt atcattatca gaagttacgc ctgtttgcgc aaccgtggcg cggacgggag   300
gcgtacgaag tggtgagacg gttgaacgag acgctgacga ggagcgcgcg agagcgatgc   360
gaaaagctcg gcggagcgtt cgcggagagt gagtgcgaat acaacgtgac gctgattaat   420
tacatggaaa cagagggtga gagcgaaata gagctacgga atgaggagaa gttcgatctc   480
gggacgacgt cggtgagttg gcacagcgat tcgtcgttgc gagaaaactc caccgtggcg   540
gtgtatcaca catacgaggc gccagagaga aaagactggc gagtggcgct gagggcgttg   600
aacgcggagt gcgaggtgct ttgcgtgcct ttggaggata agcgacgta ttacatgtgt   660
ggtgagttca cgccactca ccatcacgcc gtgctcaccg gctcgagtgc gagatattct   720
tcgacacatc gagtcgccgt ggtggccaag gatacgttcc agtacatcaa aaggcggtgt   780
atcgatgcgc tcgcaattgt accagactta gagcgcgaga ataaaccttt ggatgcgaaa   840
cagatacagt tcttagccga cgtccatcgc gaggttgaat ttcaatggat tagaatgttt   900
cacctgcaag gcgaagcaca cgcggcgtgg cacgatacgt attggacgag aaaaatcgcc   960
gagctcaccg aggcgtggga tcgcatggag gcttgctttc gagtgatttt gtccaagctc  1020
aagcgttcat ctcgctcgcc cgagtcgccg cctcgagcgt acgcgatgct gctttacgcg  1080
ctgaaaaccg tcaaggagtt gcgagacgag tacacgaagc gaaccaaggc gtcggcgtac  1140
gcgtcgctac cgccgtcgca acgtccagtt gatctgcccg cgtacgacaa tacttctccc  1200
cttccgttcg agctcaaacc cgtgatttac tttctcgagg aggagcaaaa caaagtgtga  1260
```

<210> SEQ ID NO 12
<211> LENGTH: 1257
<212> TYPE: DNA
<213> ORGANISM: Ostreococcus lucimarinus

<400> SEQUENCE: 12

```
atgagcccat cctctagcgt gctggagcct gaggatggcg agcccttcgc cagggttcat    60
cgcgctcact acaggggatt cgtggttgac gccccaagcg tgcttcctgc ttcattgcat   120
gatgacgttg agcgcgcctt cgatgacatg aggtcacgcg gagagttcac ccacgatgtg   180
gtttccgctg gtaacaaggt gtctaccact tacgttaggc gctgcctcct gggcgaggac   240
ggcatgactt accattacca gaagctccgc ctgttcgccc aaccttggag aggcagggag   300
gcttacgagg tggttagaag gctcaatgag actctgacaa gatccgcccg cgagagatgc   360
gagaagctcg gaggagcctt cgctgagtct gagtgcgagt acaacgtgac cctgatcaat   420
tacatggaga ctgagggaga gtccgagatt gagcttagaa acgaggagaa gttcgatttg   480
ggtacaacct cagtttcctg gcatagcgac tcatccctta gggagaattc aactgtggcc   540
gtttaccaca catacgaggc tcccgagcgc aaggattgga gagtggctct tagggccttg   600
aacgctgagt gcgaggtgct ttgcgttcca ttggaggaca aggccactta ctacatgtgc   660
ggcgagttca atgccacaca ccatcacgct gtgctgaccg gctctagcgc tcgctactca   720
```

```
tccactcaca gagttgccgt ggttgctaag gatacattcc agtacattaa gcgcagatgc    780
atcgatgccc ttgctattgt gccagacttg gagagggaga acaagcctct cgatgccaag    840
cagatccaat tcctggctga cgtgcatcgc gaggttgagt tccagtggat tagaatgttc    900
caccttcaag gagaggccca tgccgcttgg cacgatacct actggactag gaagatcgcc    960
gagttgaccg aggcttggga caggatggag gcttgcttcc gcgttattct ctccaagctg    1020
aagagatcta gcaggtctcc tgagagccca cctcgcgcct acgctatgct tttgtacgcc    1080
ctcaagacag tgaaggagct gagagacgag tacacaaaga ggaccaaggc ctcagcttac    1140
gcctcccttc ccccatctca gaggcccgtt gatttgccag cttacgacaa cacctctcct    1200
ctccccttcg agctgaagcc cgtgatctac ttcctggagg aggagcaaaa taaggtt      1257
```

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
atgaagcgca ccccgactg                                                 19

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
gggttttgct tccagaagct ga                                             22

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
atgaagcgga ccccgacg                                                  18

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
gggcctggtt tccagaagca g                                              21

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
atgaagcgaa ccccaaccgc                                                20

```
<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
gggtttggct tccagaagca gac                                               23

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
atgtcgccgt catcctccg                                                    19

<210> SEQ ID NO 20
<211> LENGTH: 27
<212> TYPE: DNA
<213> ORGANISM: Artificial Sequence
<220> FEATURE:
<223> OTHER INFORMATION: primer

<400> SEQUENCE: 20
cactttgttt tgctcctcct cgagaaa                                           27
```

TRANSGENIC PLANT AND THE METHOD FOR PRODUCING THE SAME

TECHNICAL FIELD

The present invention is directed to a transgenic plant and a method for producing the same. In particular, the present invention is directed to introducing a nucleic acid molecule into a plant to increase the biomass and/or yield of the plant.

INCORPORATION BY REFERENCE OF SEQUENCE LISTING

The Sequence Listing in an ASCII text file, named 35034_SequenceListing.txt of 33.6 KB, created on May 24, 2017, and submitted to the United States Patent and Trademark Office via EFS-Web, is incorporated herein by reference.

BACKGROUND

Due to the increasing population in the world, the area of the available earth for agriculture is decreasing. To increase the efficiency of agriculture and increase the diversity of the horticultural plants remains the main object of researches.

Conventional methods for improving crops and horticultural plants utilize selective breeding technologies to identify plants with desired properties. This kind of selective breeding technologies, however, has several defects: these technologies are generally labor intensive, and result in plants which generally comprise heterogeneous genetic complements which do not always transfer desired traits from the patent plants.

The development of molecular biology allows people to manipulate animals and plants. The genetic engineering of plants requires isolating and manipulating genetic materials (generally in the form of DNA or RNA) and then introducing genetic materials into plants. Such technology has resulted in plants having a variety of improved economic, agricultural or horticultural traits. A trait having special economic significance is a growth characteristic, for example, high yield.

Yield of seeds is a very important trait, for the seeds of many plants are very important to the nutrition of human being and animals. No matter via the consumption of the seeds per se or that of the meat products based on processed seeds, crops such as maize, rice, wheat and soybean, account for more than half of the total calories taken in by human. They are also origins of sugars, oils and many kinds of metabolites used for industrial processing. Based on the constant need of finding genes for increasing yield of seeds, the prior art has disclosed methods via manipulating hormone levels of plants (WO03/050287), via manipulating cell cycles (WO2005/061702) and manipulating genes involved in salt stress reactions (WO 2004/058980). In addition to yield of seeds, size of a thousand seeds, weight of a single plant, tiller number and/or plant height are also important traits for measuring yield of plants. Moreover, it should be clarified that the growth rate of a plant is not necessarily related to its yield. For example, when the fertilizer is sufficient, rice tends to grow too fast and too high during the early stage and exhibits lodging during the late stage. This leads to the decrease of yield.

Transgenic technologies introduce artificially isolated and modified genes into the genome of an organism, and lead to hereditary modifications of traits of the organism due to the expression of the introduced genes. Researches of transgenic technologies of plants mostly focus on the fields of anti-insect genetic engineering, anti-disease genetic engineering, stress resistance genetic engineering, quality genetic engineering, etc. Transgenic plants which have been commercialized are mainly anti-insect and anti-herbicide varieties. The planting of those varieties decreases the use of chemical pesticides by 37%, increases the yield of crops by 22%, and increases the profit of farmers by 68%. The current transgenic technologies, however, increase the yield indirectly by anti-insect and anti-herbicide properties, etc.

Previous researches on epigenetics generally focus on reversible modifications of DNA and histone. Recently, researchers gradually move their interest to the field of RNA modification. Up to now, scientists have discovered hundreds of RNA modifications. $N^6$-methyladenoesine ($m^6A$) is the most abundant RNA modification in mRNA across all eukaryotes. The modification of $m^6A$ has been discovered for more than forty years, but its function was not known until the inventor of the present application found the demethylase of $m^6A$, FTO protein for the first time (Jia et al, $N^6$-methyladenosine in nuclear RNA is a major substrate of the obesity-associated FTO. Nat Chem Biol, 2011, 7 (12): 885-887), reported the reversibility of RNA modification for the first time and started the "RNA epigenetics (or Epitranscriptome)" research in 2011. In 2012, researchers developed $m^6A$ antibody assisted whole transcriptome $m^6A$ high-throughput sequencing technology, $m^6A$-seq (or MeRIP). The result of the sequencing shows that there are about 12,000 $m^6A$ sites in human and mouse cells, mainly distribute on 7,000 mRNAs transcribed from encoding genes and 300 non-coding RNAs (ncRNAs) transcribed from non-coding genes (Dominissini et al, Topology of the human and mouse $m^6A$ RNA methylomes revealed by $m^6A$-seq. Nature, 2012, 485 (7397): 201-206; Meyer et al, Comprehensive analysis of mRNA methylation reveals enrichment in 3' UTRs and near stop codons. Cell, 2012, 149 (7): 1635-1646). Up to now, it has been found in the mammalian that the main components of the methyltransferase are METTL3, METTL14 and WTAP (liu et al, A METTL3-METTL14 complex mediates mammalian nuclear RNA $N^6$-adenosine methylation. Nat Chem Biol, 2014, 10 (2): 93-95; Ping et al, Mammalian WTAP is a regulatory subunit of the RNA N6-methyladenosine methyltransferase. Cell Res, 2014, 24 (2): 177-189). There are two kinds of $m^6A$ demethylases, which are FTO (fat mass and obesity associated) and ALKBH5 (Jia et al, $N^6$-methyladenosine in nuclear RNA is a major substrate of the obesity-associated FTO. Nat Chem Biol, 2011, 7 (12): 885-887: Zheng et al, ALKBH5 is a mammalian RNA demethylase that impacts RNA metabolism and mouse fertility. Mol Cell, 2013, 49 (1): 18-29). $m^6A$ regulates the metabolic processing of mRNAs, including splicing, nuclear export, stability and protein translation via $m^6A$ binding proteins.

In the plant field, researchers found that mRNAs of all plants comprise $m^6A$ extensively. It is produced by $m^6A$ modifying enzymes (currently reported modifying enzyme subunits are classified as MTA (METTL3 homologous gene) and FIP37 (WTAP homologous gene)), and has important regulatory effect on the growth and development of plants. Researchers found that when MTA or FIP37 was knocked out from Arabidopsis thaliana, the seed could not germinated normally. When MTA or FIP37 was partially complemented during the germinating stage, after germinating, the loss of $m^6A$ from Arabidopsis thaliana severely inhibited the normal growth and development of the plant (Zhong, S., Li, H., Bodi, Z., Button, J., Vespa, L., Herzog, M., and Fray, R. G (2008). MTA is an *Arabidopsis* messenger RNA adenosine methylase and interacts with a homolog of a sex-specific splicing factor. Plant Cell 20, 1278-1288; Shen, L., Liang, Z., Gu, X., Chen, Y., Teo, Z. W., Hou, X., Cai, W. M., Dedon, P. C., Liu, L., and Yu, H. (2016). $N^6$-Methyladenosine RNA Modification Regulates Shoot Stem Cell Fate in *Arabidopsis*. Dev Cell 38, 186-200).

The inventor of the present application previously found that during the demethylation process of $m^6A$ in RNA, FTO produced two relatively stable new modifications, $hm^6A$ ($N^6$-hydroxymethyladenosine) and $f^6A$ ($N^6$-formyladenosine), which had potential regulatory effect on RNA processing (Fu et al, FTO-mediated formation of $N^6$-hydroxymethyladenosine and $N^6$-formyladenosine in mammalian RNA. *Nat Commun,* 2013, 4:1798). New experimental data of the inventor showed that FTO could remove tRNA methylation modifications (the data has not been published).

It has been the task of the researches of all agriculture scientists that how to increase the yield of crops in limited area of earth to feed increasing population and how to directly and effectively increase the biomass and yield of plants. For crops (such as rice, wheat, maize), traditional transgenic technologies and hybridization breeding technologies may optimize a certain single gene, and increase the yield by 10%~30%. To achieve extremely high yield, it needs synergetic effects of many genes. The regulation of the metabolic level of mRNA by RNA methylation modification, provides the possibility of a method for regulating a single gene to achieve high yield or increase biomass.

SUMMARY OF THE INVENTION

The inventor has surprisingly found that by introducing $m^6A$ demethylase FTO into plants, the metabolic level of mRNA may be regulated, and it provides the possibility of a method for regulating a single gene to achieve high yield and/or increase biomass. To efficiently increase the yield and/or biomass of plants, the inventor introduced a heterogenous $m^6A$ demethylase by transgenic technologies, and dynamically regulate the content of $m^6A$ in mRNAs of plants so as to regulate the splicing, nuclear export, stability and protein translation of mRNAs. Compared with the traditional hybridization breeding method which increases the yield by 20-30%, with the method of the present invention, the yield of plants increased 4 folds and the biomass increased 4 folds by the regulation of a single gene. It really achieved the high yield and high biomass of plants by the regulation of a single gene.

In particular, the present invention is directed to the following aspects: In one aspect, the present invention is directed to a transgenic plant or plant cell in which a nucleic acid molecule encoding an $m^6A$ demethylase is introduced, wherein said $m^6A$ demethylase has the following two domains:

i) N-terminal domain (NTD) having the function of AlkB oxidation demethylase; and ii) C-terminal domain (CTD).

In another aspect, the present invention is directed to a method for producing a transgenic plant exhibiting an increased biomass, an increased yield (for example, increased seed/grain yield, increased tuber yield, increased leaf yield, increased stem yield, increased root yield, increased seed cotton yield) or the combination thereof, wherein said method comprises:

a) introducing a nucleic acid molecule encoding an $m^6A$ demethylase into a regenerable plant cell, wherein said $m^6A$ demethylase has the following two domains:

i) N-terminal domain (NTD) having the function of AlkB oxidation demethylase; and ii) C-terminal domain (CTD); and b) regenerating a transgenic plant from the regenerable plant cell, wherein the transgenic plant comprises in its genome said nucleic acid molecule encoding the $m^6A$ demethylase, and exhibits an increased biomass, an increased yield or the combination thereof when compared with a control plant which does not comprise the nucleic acid molecule encoding the $m^6A$ demethylase.

In one embodiment, said method further comprises:

c) obtaining a progeny plant derived from the transgenic plant of step b), wherein said progeny plant comprises in its genome said nucleic acid molecule encoding the $m^6A$ demethylase, and exhibits an increased biomass, an increased yield or the combination thereof when compared with a control plant which does not comprise the nucleic acid molecule encoding the $m^6A$ demethylase.

In one embodiment, the aforesaid $m^6A$ demethylase is a FTO protein. Said FTO protein is from vertebrates or marine algae.

In one embodiment, said FTO protein has at least 40%, preferably at least 50%, more preferably at least 60%, more preferably at least 70%, more preferably at least 80%, more preferably at least 90%, more preferably at least 95%, more preferably at least 99%, most preferably 100% identity to any one of SEQ ID NOs:1-4.

In one embodiment, said nucleic acid molecule encoding the $m^6A$ demethylase has at least 90%, preferably at least 95%, more preferably at least 99%, most preferably 100% identity to any one of SEQ ID NOs:5-12.

The transgenic plant of the present invention exhibits an increased biomass, an increased yield or the combination thereof when compared with a control plant which does not comprise the nucleic acid molecule encoding the $m^6A$ demethylase.

In one embodiment, the plant of the present invention is selected from the group consisting of rice, maize (*Zea mays*), soybean, tobacco, potato, alfalfa (*Medicago sativa*), rape (*Brassica*), Russian dandelion (*Taraxacum Koksaghyz*), cotton, wheat, millet (*Panicum miliaceum*), flax, sunflower and false flax (*Camelina saliva*) The present invention is also directed to a tissue, an organ, a pollen, a seed, a grain, a fruit and a progeny plant of the aforesaid transgenic plant.

DESCRIPTION OF THE DRAWINGS AND THE SEQUENCES

FIG. 1 shows the map of pCAMBIA1307 plasmid in which a nucleic acid encoding FTO is introduced.

SEQ ID NO: 1 is the sequence of human (*Homo sapiens*) FTO protein.

SEQ ID NO: 2 is the sequence of pig (*Sus scrofa*) FTO protein.

SEQ ID NO: 3 is the sequence of cattle (*Bos taurus*) FTO protein.

SEQ ID NO: 4 is the sequence of *Ostreococcus lucimarinus* FTO protein, from a type of marine algae, *Ostreococcus lucimarinusn.*

SEQ ID NOs: 5 and 6 are nucleic acid sequences encoding human FTO protein. SEQ ID NO:5 is the natural sequence isolated from human, and SEQ ID NO:6 is the sequence which has been codon-optimized for the expression in plants.

SEQ ID NOs: 7 and 8 are nucleic acid sequences encoding pig FTO protein. SEQ ID NO: 7 is the natural sequence isolated from pig, and SEQ ID NO: 8 is the sequence which has been codon-optimized for the expression in plants.

SEQ ID NOs: 9 and 10 are nucleic acid sequences encoding cattle FTO protein. SEQ ID NO: 9 is the natural sequence isolated from cattle, and SEQ ID NO: 10 is the sequence which has been codon-optimized for the expression in plants.

SEQ ID NOs: 11 and 12 are nucleic acid sequences encoding *Ostreococcus lucimarinus* FTO protein. SEQ ID NO: 11 is the natural sequence isolated from *Ostreococcus lucimarinus*, and SEQ ID NO: 12 is the sequence which has been codon-optimized for the expression in plants.

DETAILED DESCRIPTION OF THE INVENTION m$^6$A demethylase or the homologs thereof and the nucleic acids encoding said demethylase or the homologs may be used to produce the transgenic plant of the present invention. The m$^6$A demethylase used by the present invention may be present in any vertebrates and marine algae. Said enzyme consists of nuclear localization sequence (NLS) and the following two domains: i) N-terminal domain (NTD) having the function of AlkB oxidation demethylase; and ii) C-terminal domain (CTD).

As used herein "homolog" means a protein in a group of proteins that perform the same biological function. Homologs are expressed by homologous genes. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. Homologs are proteins that, when optimally aligned, have at least 40% identity, more preferably about 50% or higher, more preferably about 60% or higher, more preferably about 70% or higher, more preferably at least 80% and even more preferably at least 90% identity over the full length of a protein identified as increasing the yield and/or biomass of plants when expressed in plant cells.

Homologs are be identified by comparison of amino acid sequence, e.g. manually or by use of a computer-based tool using known homology-based search algorithms such as those commonly known and referred to as BLAST, FASTA, and Smith-Waterman. A local sequence alignment program, e.g. BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal query is used in the present invention to filter hit sequences with significant E-values for ortholog identification. The reciprocal query entails search of the significant hits against a database of amino acid sequences from the base organism that are similar to the sequence of the query protein. A hit is a likely ortholog, when the reciprocal query's best hit is the query protein itself or a protein encoded by a duplicated gene after speciation. A further aspect of the invention comprises functional homolog proteins that differ in one or more amino acids from those of disclosed protein as the result of conservative amino acid substitutions, for example substitutions are among: acidic (negatively charged) amino acids such as aspartic acid and glutamic acid; basic (positively charged) amino acids such as arginine, histidine, and lysine; neutral polar amino acids such as glycine, serine, threonine, cysteine, tyrosine, asparagine, and glutamine; neutral nonpolar (hydrophobic) amino acids such as alanine, leucine, isoleucine, valine, proline, phenylalanine, tryptophan, and methionine; amino acids having aliphatic side chains such as glycine, alanine, valine, leucine, and isoleucine; amino acids having aliphatic-hydroxyl side chains such as serine and threonine; amino acids having amide-containing side chains such as asparagine and glutamine; amino acids having aromatic side chains such as phenylalanine, tyrosine, and tryptophan; amino acids having basic side chains such as lysine, arginine, and histidine; amino acids having sulfur-containing side chains such as cysteine and methionine; naturally conservative amino acids such as valine-leucine, valine-isoleucine, phenylalanine-tyrosine, lysine-arginine, alanine-valine, aspartic acid-glutamic acid, and asparagine-glutamine. A further aspect of the homologs encoded by DNA useful in the transgenic plants of the invention are those proteins that differ from a disclosed protein as the result of deletion or insertion of one or more amino acids in a native sequence.

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "Percent identity" ("% identity") is the identity fraction times 100.

The m$^6$A demethylase used in the present invention may be SEQ ID NO: 1, 2, 3 or 4 of the homolog thereof. Said homolog has at least 40%, 41%, 42%, 43%, 44%, 45%, 46%, 47%, 48%, 4906, 50%, 51%, 52%, 53%, 54%, 55%, 56%, 57%, 58%, 59, 60%, 61%, 62%, 63%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%0, or 99% sequence identity to any one of SEQ ID NOs: 1-4.

The nucleic acid encoding the m$^6$A demethylase used in the present invention may be any one of SEQ ID NOs: 5-12 or the homologous gene thereof. Said homologous gene has at least 40%, 41%, 42%, 43%, 44%, 45%, 46%, 47%, 48%, 49%, 50%, 51%, 52%, 530, 54%, 55%, 56%, 57%, 58%, 59%, 60%, 61%, 62%%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 90%, 91%, 92%, 93%, 94%, 95%, 96%, 97%, 98%, or 99% sequence identity to any one of SEQ ID NOs: 5-12.

The nucleic acid encoding the m$^6$A demethylase defined herein may not be a full-length nucleic acid. A part of the nucleic acid encoding the m$^6$A demethylase defined herein may be prepared by making one or more deletions from the full-length nucleic acid.

Another nucleic acid variant used in the present invention is a nucleic acid which hybridizes with the nucleic acid encoding the m$^6$A demethylase defined herein or with a part of the nucleic acid encoding the m$^6$A demethylase defined herein under stringent conditions.

Appropriate stringent conditions which promote DNA hybridization are, for example, 6.0× sodium chloride/sodium citrate (SSC) at about 45° C., followed by a wash of 2.0×SSC at 5° C., are known to those skilled in the art or can be found in Current Protocols in Molecular Biology (1989). For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. The nucleic acid used in the present invention may specifically hybridize with a nucleic acid encoding a FTO protein, for example, any one of SEQ ID NOs: 5-12 or a part thereof under said conditions.

All or a portion of the nucleic acids of the present invention may be synthesized using codons preferred by a selected host. Species-preferred codons may be determined, for example, from the codons used most frequently in the proteins expressed in a particular host species. Therefore, the nucleic acids of the present invention include those obtained by making codon-optimization to natural FTO proteins for the expression in plants. Other modifications of the nucleotide sequences may result in mutants having slightly altered activity.

The present invention is directed to a transgenic plant in which a gene encoding the aforesaid m$^6$A demethylase FTO or a homolog thereof is introduced, or a progeny plant thereof. The present invention is also directed to a cell, a tissue, an organ, a pollen, a seed, a grain or a fruit of said plant.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores. "Progeny" comprises any subsequent generation of a plant.

According to the use, the plants of the present invention may be food crops, economic crops, vegetable crops, fruits, flowers, grasses, trees, industrial raw material crops, feed crops or medicine crops. Specifically, said food crops include rice, maize, soybean, beans, yams, potato, hulless barley, broad bean, wheat, barley, millet, rye, oat, sorghum, etc.; Said economic crops include oil tea, rape, rapeseed, flax, false flax (*Camelina sativa*), peanut, oil flax (*Linum usitatissimum*), marijuana (*Cannabis sativa*), sunflower, tobacco, cotton, beet, sugarcane, etc.; said vegetable crops include radish, Chinese cabbage, tomato, cucumber, hot pepper, carrot, etc.; said fruits include pear, apple, walnut, cherry, strawberry, jujube or peach; said flowers include flowers for view, for example, orchid, *Chrysanthemum*, carnation, rose, green plants, etc.; said grasses and trees include *Populus, Hevea brasiliensis, Taxus chinensis*, and those for urban greening or those living in deserts and harsh conditions such as drought; said industrial raw material crops include Russian dandelion, guayule, *Jatropha curcas*, etc., said feed crops include the foodstuff for livestock, such as alfalfa etc.; said drug crops include *Ginseng, Angelica* and *Ganoderma*, etc.

"Transgenic plant" includes reference to a plant which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

The present invention has prepared a DNA construct which comprises a nucleic acid molecule encoding the FTO protein described herein. The construct may comprise the nucleic acid molecule encoding the FTO protein described herein optionally operably linked to a promoter sequence which functions in a host cell. Other construct components may include additional regulatory elements, such as 5' leaders and introns for enhancing transcription, 3' untranslated regions (such as polyadenylation signals and sites), DNA for transit, signal peptides, or one or more selective maker genes.

As used herein, "promoter" means regulatory DNA for initializing transcription. A plant promoter is a promoter capable of initiating transcription in plant cells whether or not its origin is a plant cell, e.g. is it well known that *Agrobacterium* promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions. Promoters useful in the present invention are not specifically limited. Those skilled in the art may select suitable promoters according to their knowledge.

As used herein "operably linked" means the association of two or more DNA fragments in a DNA construct so that the function of one, e.g. protein-encoding DNA, is controlled by the other, e.g. a promoter.

The DNA construct generally contain a selective maker gene. Selective marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV) and gentamycin (aac3 and aacC4) or resistance to herbicides such as glufosinate (bar or pat) and glyphosate (aroA or EPSPS). Examples of such selective markers are illustrated in U.S. Pat. Nos. 5,550,318; 5,633,435; 5,780,708 and 6,118,047, all of which are incorporated herein by reference. Selective markers which provide an ability to visually identify transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

The introduction of the recombinant DNA construct into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation. For *Agrobacterium tumefaciens* based plant transformation system, additional elements present on transformation constructs will include T-DNA left and right border sequences to facilitate incorporation of the recombinant polynucleotide into the plant genome.

In general it is useful to introduce recombinant DNA randomly, i.e. at a non-specific location, in the genome of a target plant line. In special cases it may be useful to target recombinant DNA insertion in order to achieve site-specific integration, for example to replace an existing gene in the genome, to use an existing promoter in the plant genome, or to insert a recombinant polynucleotide at a predetermined site known to be active for gene expression. Several site specific recombination systems exist which are known to function in plants include cre-lox as disclosed in U.S. Pat. No. 4,959,317 and FLP-FRT as disclosed in U.S. Pat. No. 5,527,695, both incorporated herein by reference.

Transformation methods of this invention are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants of this invention, for example various media and recipient target cells, transformation of immature embryo cells and subsequent regeneration of fertile transgenic plants are disclosed in U.S. Pat. Nos. 6,194,636 and 6,232,526, which are incorporated herein by reference.

The development or regeneration of plants containing the foreign, exogenous isolated nucleic acid fragment that encodes a protein of interest is well known in the art. The regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing the nucleic acid molecule encoding the FTO protein is cultivated using methods well known to one skilled in the art.

The seeds of transgenic plants can be harvested from fertile transgenic plants and be used to grow progeny generations of transformed plants of this invention including hybrid plants line for selection of plants having an enhanced trait. In addition to direct transformation of a plant with the nucleic acid molecule encoding the FTO protein, transgenic plants can be prepared by crossing a first plant having the nucleic acid molecule encoding the FTO protein with a second plant lacking the nucleic acid molecule. For example, the nucleic acid molecule encoding the FTO protein can be introduced into first plant line that is amenable to transformation to produce a transgenic plant which can be crossed with a second plant line to introgress the nucleic acid molecule encoding the FTO protein into the second plant line. The transgenic plant derived from the plant cell of the present invention is cultivated to produce increased yield and/or biomass compared with a control plant. As used herein a "control plant" means a plant that does not contain the nucleic acid molecule encoding the FTO protein. A control plant is to identify and select a transgenic plant that has increased yield and/or biomass. A suitable control plant can be a non-transgenic plant of the parental line used to generate a transgenic plant, i.e. devoid of the nucleic acid molecule encoding the FTO protein. A suitable control plant may in some cases be a progeny of a hemizygous transgenic plant line that does not contain the nucleic acid molecule encoding the FTO protein, known as a negative segregant.

The "yield" of the transgenic plant described herein means the harvest amount of the product desired by the cultivation. The standards for evaluating the yields of different plants are different. For example, the subject of the evaluation of the yields of cereal crops (rice, wheat, maize, etc.), beans and oil crops (soybean, peanut, rape, etc.) is the seed (grain); that of cotton is the seed cotton or the lint cotton; that of yam crops (sweet potato, potato, cassava, etc.) is the tuberous root or tuber; that of bast fiber crops is the fiber of stems or the fiber of leaves; that of sugarcane is the stem; that of beet is the root; that of tobacco is the leaf; that of green manure crops (alfalfa, trefoil, etc.) is the stem and leaf, etc. The meaning of the yield of the same plant differs when it is cultivated for different purposes. For example, when maize is cultivated as food and fine feed crop, the yield is the harvest amount of grains, and when it is cultivated as silage, the yield includes the total harvest amount of stems, leaves and ears. The increased yield of the transgenic plant of the present invention may be measured by many means, including measuring weight, seed number per plant, seed weight, tuber weight, seed number per unit area (i.e. seeds, or weight of seeds, per acre), bushels per acre, tonnes per acre, tons per acre, kilo per hectare.

Those skilled in the art can determine the meaning of the yield for each plant and the standard for evaluating it according to the knowledge in the art.

Biomass means the total mass of the existing organic materials of an organism. It is expressed as dry weight, fresh weight, tiller number, etc. in the present invention. The increased biomass of the transgenic plant of the present invention may be measured by many means, including measuring weight, dry weight or fresh weight of the overground parts per plant, tiller number, dry weight of the overground parts per unit area (i.e. dry weight or fresh weight, per acre), bushels per acre, tonnes per acre, tons per acre, kilo per hectare.

EXAMPLES

The present invention is further illustrated in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Furthermore, various modifications of the invention in addition to those shown and described herein will be apparent to those skilled in the art from the foregoing description. Such modifications are also intended to fall within the scope of the appended claims.

The materials used in the following examples were as follows:
1. Formulation of YEP broth for the growth of *Agrobacterium* (per liter): yeast extract 10 g/L+peptone 10 g/L+NaCl 5 g/L, PH 7.2. For the solid medium, 15 g/L agar was added.
2. *Agrobacterium* re-suspension AAM broth: 50 ml 20×AA macroelement, 10 ml 100×FeEDTA, 10 ml 100×B5 macroelement, 10 ml 100×B5 vitamin, 100 ml 10×AA amino acid, 1 ml 100 mM acetosyringone, 68.5 g sucrose, 36 g glucose, 0.5 g hydrolyzed casein. The volume was adjusted to 1000 ml. The pH was adjusted to 5.2. Sterilized with a 0.2 mm cellulose acetate membrane.
3. 20×AA macroelement: 59 g KCl, 3 g $CaCl_2.2H_2O$, 10 g $MgSO_4.7H_2O$ and 3 g $NaH_2PO_4.H_2O$. The volume was adjusted with distilled water to 1 L. Stored at 4° C.
4. O1×AA amino acid: 8.76 g Gin, 2.66 g Asp, 1.74 g Arg and 75 mg Gly. The volume was adjusted with distilled water to 1 L. Sterilized with a 0.2 mm cellulose acetate membrane. Stored at 4° C.
5. 10 ml 100×B5 vitamin: 10 g myoinositol, 1 g thiamine hydrochloride, 100 mg pyridoxine hydrochloride and 100 mg nicotinic acid. The volume was adjusted with distilled water to 1 L. Stored at 4'C.
6. 100×B5 macroelement: 1.320 mg $MnSO_4.4H_2O$, 200 mg $ZnS_4.7H_2O$, 2.5 mg $CuSO_4.5H_2O$, 25 mg $Na_2MoO_4.2H_2O$, 2.5 mg $CoCl_2.6H_2O$, 300 mg $H_3BO_3$ and 75 mg KI. The volume was adjusted with distilled water to 1 L. Stored at 4° C.
7. NB medium: macroelements and microelements of N6 medium, organic elements of B5 medium, 300 mg/L hydrolyzed casein, 500 mg/L glutamine, 30 g/L sucrose and 8 g/L agar.

Example 1: Obtaining cDNA of the $m^6A$ Demethylase Gene

The FTO genes were searched from the database of National Center for Biotechnology Information (NCBI). Amino acid sequences (SEQ ID NOs: 1-4) and nucleic acid sequences (SEQ ID NOs: 5, 7, 9 and 11) of human (*Homo sapiens*) FTO, pig (*Sus scrofa*) FTO, cattle (*Bos Taurus*) FTO and alga (*Ostreococcus lucimarinus* CCE9901) FTO were obtained. The corresponding cDNAs were purchased, or synthesized by GenScript when there are no commercialized cDNAs. The amino acid sequences of SEQ ID NOs: 1-4 were optimized to plant codons to synthesize the codon-optimized nucleic acid sequences SEQ ID NOs: 6, 8, 10 and 12.

The FTO gene cDNAs used in the following examples are SEQ ID NO:5, 7, 9 and 11.

Example 2: Cloning the $m^6A$ Demethylase Gene

The FTO gene cDNAs (SEQ ID NO:5, 7, 9, 11) were cloned into the plant binary vector pCAMBIA1307. The average size of the inserted gene sequences was 1.5 kb. The obtained plasmid is shown in FIG. 1.

Example 3: Transformation of the Plants 3.1 Introduction of the FTO Gene of Example 2 into Rice with the Transgenic Technologies 1. Inducing Calluses with Mature Embryos of Rice as Test Materials 1. Sterilization Mature seeds of rice (*Japonica* Nipponbare) were artificially unshelled. Seeds which were full, bright and clean, and bacterial plaque free were selected and placed into a 100 ml sterilized flask. 70% alcohol was added into the flask to sterilize for 2 minutes. Then, the alcohol was decanted, and 20% NaClO was added to soak for 30 minutes. Then, the NaClO was decanted, and the seeds were rinsed 4-5 times with sterilized distilled water. Lastly, the seeds were soaked with sterilized distilled water for 30 minutes.

2. Introduction Culture (Under Aseptic Conditions):

The sterilized seeds were placed on sterilized filter paper. After the water on the surface were absorbed by the filter paper, the seeds were placed into NB medium (PH5.8) containing 2.0 mg/L 2, 4-D at the density of 12-14 seeds per petri dish. To ensure good induction rate, the germination orientation of the seeds was made parallel to the medium or slightly downward, and not upward or vertically upward. Then, the petri dish was sealed with membrane, and was induced and incubated for 20-30 days in an incubator with light at 30° C., 50% humidity until obviously loose calluses appeared. Then, subculture was performed.

3. Subculture (Under Aseptic Conditions):

The petri dish was opened on a super-clean operating desk. Calluses which naturally divided, grew vigorously and which were hard and bright yellow and which had the diameter of about 3 mm were placed in NB medium (PH5.8) containing 2.0 mg/L 2,4-D and 0.5 mg/L 6-BA at the density of 10 calluses per petri dish, and were dark incubated at 30° C. If the calluses seriously turned soft, they were moved into light to be subcultured. The subculture was performed twice, each 10-15 days (the time of the next subculture was determined according to how much the calluses grew).

II. The Culture of the *Agrobacterium*

The pCAMBIA1307 vector carrying FTO gene and Hygromycin resistance gene shown in FIG. 1 was transfected into *Agrobacterium* LBA4404. Then, *Agrobacterium* LBA4404 was seeded into YEP solid medium containing 20 mg/L Rifampin (Rif) and SOmg/L kanamycin (Kan). After cultured at 28° C. for two days, *Agrobacterium* monoclones were picked up to be subject to colony PCR to test whether the FTO was transferred into the *Agrobacterium*. Positive monoclones were selected and placed in 4 ml YEP (containing 50 mg/L Kan and 20 mg/L Rif) broth, and were shaking-cultured at 28° C., 220 rpm for 20-36 h until the $OD_{600}$ of the bacterial solution was 0.8-1.0.

III. Infection and Co-Culture

1. The solution of the cultured *Agrobacterium* was centrifuged at 4° C., 4000 rmp for 10 min, and was made to suspension with AAM broth containing 100 μmol/L acetosyringone. The final OD$_{600}$ of the bacterial solution was about 0.2.

2. The calluses with certain size was picked up and placed into the suspension of the *Agrobacterium* to be infected for 20-30 min.
3. The calluses were took out and placed on sterilized filter paper to be dried for 20-30 min so as to prevent undue injury of the calluses caused by the over-growth of the *Agrobacterium* during the co-culture.
4. The calluses were placed in NB medium (PH5.2) containing 2.0 mg/L 2,4-D and 100 μmol/L acetosyringone and were cultured at 25° C. for 48-72 h in the dark.

IV. Screening of Calluses with Resistance

The calluses were took out and rinsed with shaking by sterilized water for 5-6 times. Then, the calluses were placed on sterilized filter paper to be dried and then placed evenly in NB medium (PH 5.8) containing 50 mg/L hygromycin for the first screening. The calluses were cultured in the dark at 28° C. and when there was growth of mold or *Agrobacterium*, the calluses were timely moved to a new screening plate.

After screening for about 30 days, new calluses were produced. They were moved to new NB medium (PH 5.8) containing SOmg/L hygromycin for another 7-10 day screening. If the growth was obvious, they were positive calluses. If there was no growth (even if there was no browning or death), they were possibly false positive.

V. Introducing the Differentiation of the Calluses with Resistance and Rooting

The vigorously grew, yellow calluses after the second screening (to ensure that the calluses used to differentiate were not defective) were placed in NB medium (PH 5.8) containing 2.0 mg/L 6-BA, 0.5 mg/L kinetin, and 50 mg/L hygromycin at the density of 2-3 positive clones per bottle. It was enough to place a little of calluses per clone. The placed calluses should have high quality rather than large number. After cultured at 27° C. in the dark for 10 days, they were allowed to differentiate in the light for 10-20 days. After green leaves appeared, they were allowed to root at the light density of 4000 lux, 14 h/d.

The strong seedlings differentiated from each clone were placed in ½N6 medium (PH5.8) containing 0.5 mg/L naphthaleneacetic acid and 50 mg/L hygromycin to induce rooting at the density of 2-3 seedlings each bottle. The seedlings were cultivated at 27-30'C in the light at the light density of 4000 lux, 14 h/d. After 7-10 days, the sealing membranes were opened to add appropriate amount of water. After 2-3 days, the seedlings were transplanted.

VI. Training and Transplantation of the Transgenic Seedlings

The rice seedlings with well differentiated roots, stems and leaves were picked up (when the seedlings grew to the top of the test tubes, the covers should be opened timely). The sealing membranes were opened and appropriate amount of distilled water or sterilized water was added (to prevent the growth of bacteria in the medium). The seedlings were trained for about 3 days to one week. After the agar was rinsed, the seedlings were transplanted into earthen bowls in the greenhouse to grow and to be tested.

Example 4 Test of the Transformed Seedlings

1. PCR detection: The design of FTO gene primers

Primers for detecting human FTO (hFTO):

(SEQ ID NO: 13)
hFTO-F: 5'-ATGAAGCGCACCCCGACTG-3';

(SEQ ID NO: 14)
hFTO-R: 5'-GGGTTTTGCTTCCAGAAGCTGA-3';

Primers for detecting cattle FTO (cFTO):

(SEQ ID NO: 15)
cFTO-F: 5'-ATGAAGCGGACCCCGACG-3';

(SEQ ID NO: 16)
cFTO-R: 5'-GGGCCTGGTTTCCAGAAGCAG-3';

Primers for detecting pig FTO (pFTO):

(SEQ ID NO: 17)
pFTO-F: 5'-ATGAAGCGAACCCCAACCGC-3';

(SEQ ID NO: 18)
pFTO-R: 5'-GGGTTTGGCTTCCAGAAGCAGAC-3';

Primers for detecting *Ostreococcus lucimarinus* FTO (olFTO):

(SEQ ID NO: 19)
olFTO-F: 5'-ATGTCGCCGTCATCCTCCG-3';

(SEQ ID NO: 20)
olFTO-R: 5'-CACTTTGTTTTGCTCETCCTCGAGAAA-3'.

The PCR reaction program was: 35 cycles of 95° C. 5 min, 95° C. 15 s, 58° C. 15 s, 72° C. 30 s. Extended at 72° C. for 10 min, stored at 4° C. After the reaction, PCR products were subject to 1% agarose gel electrophoresis analysis.

2. Method for rapidly detecting the transgenic seedlings: the freshly green leaves of about 1 cm were cut and collected from the seedlings to be tested (both sides had incisions) and were placed flatly on the test medium (0.7% agar, 1 ml/L 6-BA, 50 mg/L hygromycin) and were cultured at 28° C. for 48 h (16 h light/8 h dark each day). The plants which have freshly green leaves were positive ones while the leaves of the negative seedlings had plaques of necrosis.

Example 5 Evaluation of the Effects of FTO Genes from Several Species in Rice

The test results of the rice of example 3 are shown in table 1 (the *Japonica* Nipponbare variety which had not been introduced the FTO gene was the control). The data were obtained from 50 transgenic and control rice plants in maturation stage. Dry weight was weighed after placed in 105° C. oven for 20 mins and 80° C. oven for 20 hours.

TABLE 1

Evaluation of the effects of human, cattle, pig and *Ostreococcus lucimarinus* FTOs introduced into rice (transgenic plants/control plants)

| The introduced nucleic acids encoding the FTOs | Plant | Tiller number Increased folds | Fresh weight of the seeds Increased folds | Dry weight of the seeds Increased folds | Biomass of the whole plant (seeds plus the overground parts) Increased folds | Biomass (fresh weight of the overground parts after removing the seeds) Increased folds | Biomass (dry weight of the overground parts after removing the seeds) Increased folds |
|---|---|---|---|---|---|---|---|
| Human FTO (SEQ ID NO: 5) | rice | 2.54 | 4.58 | 4.15 | 2.61 | 2.41 | 3.87 |
| Cattle FTO (SEQ ID NO: 7) | | 2.15 | 4.15 | 3.71 | 2.37 | 2.22 | 3.61 |
| Pig FTO (SEQ ID NO: 9) | | 2.08 | 4.02 | 3.62 | 2.34 | 2.11 | 3.60 |
| *Ostreococcus lucimarinus* FTO (SEQ ID NO: 11) | | 1.85 | 3.78 | 3.41 | 2.51 | 2.15 | 3.45 |

Table 1 shows that after the nucleic acids encoding the FTOs of several species were introduced to rice, the biomass and the yield of seeds were increased.

The inventor also tested the codon-optimized nucleic acids encoding the FTOs (SEQ ID NOs:6, 8, 10 and 12) by the same method. The data are similar to the above, and thus are not shown herein.

Example 6 Evaluation of the Effect of FTO in a Variety of Plants

A variety of plants were transformed with the nucleic acid encoding human FTO (SEQ ID NO:5) to obtain a variety of transgenic plant cells and plants in which the nucleic acid encoding the FTO were introduced. The methods are as follows:

Genetic Transformation Method of Tobacco

1. Experimental Materials

Materials: Tobacco variety: K326; *Agrobacterium*: LBA4404; HF (human FTO) gene was cloned into the 35S promoter-driven vector pCAMBIA2300. The screened resistance in eukaryotic plants was resistance to Kanamycin.

Chemicals: MS macroelements, MS microelements, MS iron salts, indole acetic acid (IAA), 6-benzylaminoadenine (6-BA), inositol nicotinate ($B_1B_6$), sucrose, agar, cephalosporin (Cef), carbenicillin (Carb), kanamycin (Kn), gentamicin, rifampicin; MS medium (1 L): macroelements (20×) 50 ml, microelements (100×) 10 ml, $Fe^{2+}$ (100×) 10 ml, sucrose 30 g, agar 8 g. The pH was about 6.0.

Pre-culture medium (1 L): macroelements (20×) 50 ml, microelements (100×) 10 ml, $Fe^{2+}$ (100×) 10 ml, 6-BA (1000×) 2 ml, $B_1B_6$ (200×) 5 ml, glycine (1000×) 1 ml, agar 8 g. The pH was about 6.0. After high temperature sterilization, IAA (0.2 mg/L) 1 ml was added.

Differentiation culture medium (1 L): based on the pre-culture medium, cephalosporin 2 ml, carbenicillin 1 ml and kanamycin 1 ml were added.

Rooting culture medium (1 L): ½MS, IAA 2 mg/L, sucrose 30 g/L, agar 5.8 g/L, pH=5.8

LB broth (1 L): tryptone 10 g, yeast extract 5 g, NaCl 10 g.

$MS_0$ medium: MS culture medium without the addition of agar and only containing macroelements 2. Tobacco Transformation (Leaf Disc Method)

Tobacco was transformed by leaf disc method. The cut tobacco leaf discs were placed on the pre-culture medium for 1-2 days, and then soaked in *Agrobacterium* suspension ($MS_0$ suspended, diluted by 50-100 times) for 3-5 minutes. Then, the discs were taken out, and sterile filter paper was used to absorb the liquid on their surfaces. The infected leaf discs were respectively inoculated on a pre-culture medium covered with two layers of filter paper and cultured at 26° C. for 20-24 h in dark. The discs were rinsed with the sterilized water added with cephalosporin and carbenicillin (1000 times the mother liquor) for 10 min. The, they were finally rinsed with sterilized water for 10 min. Subsequently, sterile filter paper was used to absorb the liquid on their surfaces, and then the discs were placed in the differentiation culture medium for differentiation culture. In the early stages, subculturing was performed every 2-3 says, and each subculturing shall be carried out under aseptic conditions; after the continual subculturing for three times, subculturing was performed every two weeks. Co-culture was carried out until the first bud appeared. The buds were transferred into tissue culture vessels for culturing. When the buds grew to 2 cm, all the calluses at basal parts of buds and basal leaves were cut on a super-clean operating desk, and then the buds were placed in the rooting culture medium. When the roots grew to 3 cm, sterile seedlings were taken out; the solid culture medium was smashed gently, while the residual culture medium was rinsed off. Thereafter, the sterile seedlings were placed in soil, covered with clear plastic bags (pricked), and cultured for about one week, and then transferred outdoors (growing in dark in the first 3 days).

Transformation Method of Potato

1. Materials:

Potato variety: Dongnong 303; *Agrobacterium*: LBA4404; HF (human FTO) gene was cloned into the 35S promoter-driven vector pCAMBIA2300. The screened resistance in eukaryotic plants was resistance to Kanamycin.

2. Potato Transformation

The potatoes were cleaned by rinsing with distilled water, soaked with 75% alcohol for 30 sec, soaked with 0.1% mercuric chloride for 10 min, cleaned with sterilized water for 5 times, and then peeled to be cut into slices with the thicknesses around 1 mm. The slices were mixed with the *Agrobacterium* solution under gentle shaking to enable the *Agrobacterium* solution to contact with the explants sufficiently. Sterile filter paper was used to absorb the redundant *Agrobacterium* solution. Then the potato pieces were placed in the co-culture medium for dark culture. After the completion of co-culture, the potato pieces were cleaned for 3 times with sterilized water and liquid MS culture medium respectively. The redundant *Agrobacterium* solution was rinsed off. The potato pieces were transferred into the regeneration culture medium. Then, the potato pieces were transferred into the rooting culture medium till the buds grew to 1.5-2.0 mm and were cut, for rooting screening propagation.

Genetic Transformation of Soybean

1. Materials

*Agrobacterium* strain was LBA4404; somatic cell embryo masses of soybean Dongnong L13 at the globular stage; the transgenic plasmid was a 35S promoter-driven vector pCAMBIA2300 into which the HF gene was cloned. The screened resistance in eukaryotic plants was resistance to kanamycin.

Plant Tissue Culture Medium and Culture Conditions:

Subculture medium: MS+15 mg/L)–20 mg/L 2,4-D+0.8% agar+3% sucrose pH=5.8 natural light Re-suspension culture medium: subculture medium (liquid)+AS (0-100 μmol/L) pH=5.8 Natural light Co-culture medium: infection culture medium+AS (0-100 μmol/L) pH=5.6

Sterilization screening culture medium: subculture medium+(50-300 mg/L) cephalosporin+25-50 mg/L kanamycin Germination culture medium 1: M S+1% activated carbon+0.8% agar+10% sucrose illumination 16 h/d Germination culture medium 2: MS+0.8% agar+10% sucrose illumination 16 h/d seedling strengthening culture medium: MSB+0.8% agar+3% glucose pH=7 illumination 16 h/d (into the last three culture media, Kanamycin 0-50 mg/L L and cephalosporin 0-300 mg/L were added at the same time)

2. *Agrobacterium* Infected Transformation and Plant Regeneration

The somatic cell embryo masses of soybean with the diameters around 3 mm were placed in the prepared *Agrobacterium* infection liquor for infection. Then, the bacterial solution was poured away, and the sterile filter paper was used to absorb the redundant liquid to dry the embryo masses. Thereafter, the embryo masses were inoculated onto the co-culture medium, then onto the sterilization screening culture medium containing 50 mg/L of Kanamycin and 300 mg/L of cephalosporin (the concentrations decreased in sequence depending upon the situation, with the proviso that no bacteria grew). The infection time was 10 min. The co-culture time was 2 to 3 days. Acetosyringone was 100 μmol/L. The *Agrobacterium* concentration OD600 was 0.5-0.7. Subculturing was performed every 15 to 20 days. The number of the resistant somatic cell embryo masses (with the diameters around 3 mm) as generated was inspected within 3 months. The transformation ratio (the number of the resistant somatic cell embryo masses/the number of the inoculated somatic cell embryo masses×100) was calculated. Then, the resistant somatic cell embryo masses were transferred into the germination culture medium 1, and then into the germination culture medium 2 after 20 days of germination. Till the regenerated resistant small plants were grown, said plants were transferred into the seedling strengthening culture medium to obtain the transformed plants.

Genetic Transformation of Alfalfa

1. Materials

Alfalfa variety; Gongnon-1; *Agrobacterium*: LBA4404; a plant binary expression vector pCAMBIA2300 into which the HF gene was cloned and resistant to Kanamycin.

The culture medium was a MS culture medium added with various growth regulating substances, with a pH value of about 5.8. The culture temperature was 23 to 25° C. The illumination intensity was 2 000 lx; the illumination time was 18 h/d. The subculturing was performed about every 20 d.

2. Preparation of Calluses

The hypocotyls were used as explants to undergo callus induction, and somatic embryo differentiation. After the somatic embryos were mature, somatic embryos were transferred into $MS_0$ for germination test.

3. Suspending Culture of Embryogenic Calluses 3 g of calluses were inoculated into a 150 mL erlenmeyer flask containing 40 mL of suspending culture solution for performing suspending culturing. A fresh culture medium was used for change every 7 d. The rotational speed of the shaker was 150 r/min. Natural scattering light was used for illumination. After 15 d, the cell growth speed was determined. The suitable calluses were inoculated into the best embryogenic callus induction broth that had been screened out. The rotational speed of the shaker was set as 120 r/min. A fresh culture medium was used for change every 7 d. The illumination with natural scattering light lasted about 30 d.

4. *Agrobacterium* Transformation

Embryogenic calluses were placed in a 2.0 mL small centrifuge tube containing 600 μL of liquid co-culture medium for the ultrasonic wave treatment of 8 s with a parameter of 100 m Hz and the subsequent co-culture of 4 d. The infected suspending embryogenic calluses were placed flatwise in a semi-solid co-culture medium containing 100 μmol/L of acetosyringone for dark culture of 4 d.

5. Screening and Regeneration of Transformed Plants

The co-cultured embryogenic calluses were inoculated into the differentiation culture medium for culturing of 50 to 60 d. After 4 embryonic stages, embryogenic calluses grew into mature somatic embryos. Then, they were transferred into a somatic embryo germination culture medium. After about 20 to 30 d, when the plants grew to about 10 cm, the seedlings were transplanted, wherein the used Kanamycin screening concentration was 30 mg/L.

Genetic transformation of Rape

1. Materials

Cabbage type rape variety CY2 for genetic transformation; *Agrobacterium* strain EHA105; a plant binary expression vector pCAMBIA1301 into which the HF gene was cloned.

2. *Agrobacterium* Transformation

Fresh bacterial colonies were selected by toothpick to be cultured in a YEB broth containing Km 50 mg/L and Rif 50 mg/L under shaking at 28° C., till logarithm dividing middle stage (OD600=0.3). The bacterial solution was taken for centrifugation at 12 000 r/min for 1 min, washed once with MS culture medium under centrifugation, and then diluted by 10 times. The recipient parent CY2 seeds were sterilized and inoculated onto a ½ MS culture medium for culturing sterile seedlings. After 5-7 d, hypocotyls were cut into small sections about 1 cm long to serve as explants for the *Agrobacterium tumefaciens* mediated transformation with the plasmid pCAMBIA1301 carrying HF gene. The transformation was carried out following the method of Wang Fulin et al. (Journal of Nuclear Agricultural Sciences, 5(26): 1129-1134(2011)). Transformants were screened by hygromycin (Hyg) 10 mg/L. The screened Hyg resistant seedlings rooted, and were domesticated in greenhouse pots for a period of time, and then transplanted into fields.

Genetic Transformation of Cotton

I. Materials and Reagents

Cotton variety: Zhong 521; *Agrobacterium* strain GV3101; a plant binary expression vector pCAMBIA2300 into which the HF gene was cloned and resistant to Kanamycin.

MBS culture medium: MS inorganic ingredient+B5 organic ingredient as the basic culture medium, added with different hormone ingredients;

Infection liquor. MS inorganic salts+B5 organics+0.1 mg/L 2,4-D+0.1 mg/L KT+100 μmol/L AS (acetosyringone)+30 g/L glucose;

Co-culture: MS inorganic salts+B5 organics+0.1 mg/L 2,4-D+0.1 mg/L KT+100 μmol/L AS (acetosyringone)+30 g/L glucose+2.5 g/L plant gel;

Screening culture medium: MS inorganic salts+B5 organics+0.1 mg/L 2,4-D+0.1 mg/L KT+30 g/L glucose+2.5 g/L plant gel+Kanamycin 50 mg/L+150 mg/L carbenicillin 2. Culturing of Explants The cotton seeds delinted with concentrated sulfuric acid were cleaned with tap water; seed kernels were taken out. Then, the delinted seeds were placed into a sterilized erlenmeyer flask on a super-clean operating desk. The seeds were soaked with 70% to 75% alcohol for 1 min, rinsed with sterilized water, and then soaked with 2% sodium hypochlorite for 60 min. Thereafter, sodium hypochlorite was poured away, and the seeds were rinsed with sterilized water for many times, and soaked in sterilized water for 24 h. After the seeds were revealed, the seed coats were peeled off. The seeds were inoculated into a ½ MS seedling culture medium for dark culture at 28° C. The seedlings at the age of 5 d or so were taken to be cut into small pieces of 0.5-0.6 cm to serve as explants.

3. Co-Culture of Explants and *Agrobacterium*

Hypocotyls of sterile seedlings were cut into small sections of 0.5 cm or so, and soaked in *Agrobacterium* solution for 30 to 40 min. Sterile filter paper was used to absorb the bacterial solution. Said small sections were placed on a MSB solid culture medium for co-culture of 48 h.

4. Induction and Selection of Calluses and Plant Regeneration

The co-cultured hypocotyl cuts were transferred into the MSB solid screening culture medium containing 50 mg/L of kanamycin and 500 mg/L of carbenicillin. Till the culture lasted 60 d, the positive callus masses resistant to Kanamycin were selected to be transferred into the above culture medium free of antibiotic for subculturing. Thereafter, according to the state of calluses, particulate embryogenic calluses were obtained by adjusting the hormone concentration in the culture medium, and then embryoids were differentiated to culture regenerated plants.

Genetic Transformation of Wheat (Embryogenic Calluses)

1. Test Materials

Immature embryo tissues were used for culturing. The test variety was Henong 827. *Agrobacterium* strain C58. A plant binary expression vector pCAMBIA2300 into which the HF gene was cloned and resistant to Kanamycin.

The culture media used in the genetic transformation process of wheat included:

Callus induction culture medium MSW0: MS basic medium+2 mg/L 2,4-D+4 mg/L picloride+0.5 g/L glutamine+0.75 g/L MgCl$_2$+0.1 g/L hydrolyzed casein+1.95 g/L MES+100 mg/L ascorbic acid+40 g/L maltose+4.5 g/L agar, pH 5.8;

Infection liquor PCM: MS basic medium+2 mg/L 2,4-D+4 mg/L picloride+0.5 g/L glutamine+0.75 g/L MgCl$_2$+0.1 g/L hydrolyzed casein+1.95 g/L MES+100 mg/L ascorbic acid+200 μmol/L acetosyringone+40 g/L maltose+4.5 g/L agar, pH 5.8;

Callus screening culture medium SM: MS basic medium+2 mg/L 2,4-D+4 mg/L picloride+0.5 g/L glutamine+0.75 g/L MgCl$_2$+0.1 g/L hydrolyzed casein+1.95 g/L MES+100 mg/L ascorbic acid+250 mg/L carbenicillin+25 mg/L G418+40 g/L maltose+4.5 g/L agar, pH 5.8;

Resistant callus differentiation culture medium RSM: MS basic medium+2 mg/L 2,4-D+4 mg/L picloride+0.5 g/L glutamine+0.75 g/L MgCl$_2$+0.1 g/L hydrolyzed casein+1.95 g/L MES+100 mg/L ascorbic acid+250 mg/L carbenicillin+25 mg/L G418+0.5 mg/L kinetin+0.2 mg/L naphthalene acetic acid+40 g/L maltose+4.5 g/L agar, pH 5.8;

2. Sterilization of Immature Grains and Inoculation of Immature Embryos

The immature grains were taken 12 to 15 days after pollination of wheat to be surface-sterilized with 70% alcohol for 30 s, sterilized with 0.1% mercuric chloride for 8 min, and cleaned with sterilized water for 4-5 times. Immature embryos were picked out with dissecting needles, and were respectively inoculated onto the callus induction culture medium MSW0 with scutum upwards, for dark culture of 2 weeks at 25° C., and then transferred into the differentiation culture medium for illumination of 16 h at 25° C. and dark culture of 8 h for 4-6 weeks.

3. *Agrobacterium*-Mediated Genetic Transformation Procedures

The *Agrobacterium* C58 containing HF was inoculated uniformly with applicator onto the LB solid culture medium (pH 7.0, containing 50 mg/L of kanamycin and 50 mg/L of rifampicin) for culturing of 3 d at 28° C. and then culturing of 1 d at 23° C. Thereafter, a minor amount of *Agrobacterium* was scraped from the culture medium to be transferred and inoculated into the YEP broth containing the aforesaid antibiotic for overnight culture at 28° C., at the shaker rotational speed of 250 r/min. *Agrobacterium* was collected till OD600 reached 1.0, and was re-suspended with PCM infection liquor. The re-suspension was used to soak calluses for 3 h. Then, the bacterial solution was poured away. The calluses were transferred into the culture dish spread with sterile filter paper for co-culture of 3 d, then transferred into the screening culture medium for dark culture of 2 weeks at 25° C., and then transferred into the differentiation culture medium for illumination culture at 25° C.

Genetic Transformation of Millet

The same method as wheat was used.

Genetic Transformation of Flax

1. Materials

Flax: Heiya 7; *Agrobacterium tumefaciens* strain EHA105; a plant binary expression vector pCAMBIA1301 into which the HF gene was cloned and resistant to Kanamycin.

2. Preparation of Explants

Filled and shiny seeds Heiya 7 were selected, soaked with 75% alcohol for 5 min, soaked with 20% bleach powder supernatant for 20 min, rinsed with sterilized water for three times, and then inoculated onto the MS culture medium for dark culture of 5-7 d at 25° C. 2 days before application, the seeds were placed under illumination for 16 h each day at 22° C. for use.

3. Preparation of *Agrobacterium* Bacterial Solution

The propagation of strain EHA105 containing the gene of interest was performed using a YEP culture medium, peptone 10 g/L, yeast extract 10 g/L, NaCl 5 g/L, and kanamycin 50 mg/L. After inoculation, shaking culture was carried at 28° C. for 2 d. Top phase was removed by centrifugation for 10 min at 3000 r/min. The bacteria was suspended with a ½ MS broth (OD600=0.5) for transformation.

4. Selective Pressure Test

The sterile flax hypocotyls were cut into small pieces of 0.3-0.5 mm. Said small pieces were soaked with sterilized water for 10 min, absorbed dry by sterile filter paper, and respectively inoculated onto the MS culture medium of kanamycin 50 mg/L for culture at 24-26° C. The illumination period was 16 h each day.

5. Co-Culture

The flax hypocotyls were cut into small pieces of 0.3-0.5 mm. Said small pieces were soaked with *Agrobacterium* EHA105 suspension for 10-20 min, absorbed dry by sterile filter paper, and respectively inoculated onto the MS, B5 or N6 culture medium of KT 2 mg/L, IAA 3.5 mg/L or HL 150 mg/L. The culture conditions were the same as above.

6. Screening Culture and Rooting

The screening culture medium was the same as that for co-culture, and only differed in the addition of 50 mg/L of kanamycin and 1000 mg/L of cephalosporin. The explants co-cultured for 3 days with *Agrobacterium* were soaked with 2000 mg/L of cephalosporin solution for 10-20 min, absorbed dry by sterile filter paper, and then inoculated onto the screening culture medium for culture under the same conditions as shown above. The sterilization and callus formation were inspected one week and two weeks after inoculation respectively. The selected resistant buds were transferred onto the rooting culture medium for induced rooting.

Genetic transformation of Sunflower

1. Materials

Helianthusannuus Xinkuiza 6; *Agrobacterium tumefaciens* strain EHA105; a plant expression vector pCAMBIA1301 into which the HF gene was cloned.

2. Strain Culturing

Fresh *Agrobacterium tumefaciens* single colonies were selected to inoculate into a YEP (1% yeast extract+1% tryptone+0.5% beef extract) broth under shaking at 28° C. overnight. On the next day, they were transferred and inoculated into a 20 mL YEP broth containing antibiotic at 1% inoculation amount for the further vibration and culture till logarithm growth period; bacteria were collected by centrifugation and diluted by MES liquid till $OD_{600}$ reached 0.8 as the working concentration for use.

3. Culture Media $MS_0$ medium: MS basic ingredients+2% sucrose+0.8% agar, pH 5.8;

GBA basal medium: $MS_0$+0.5 mg/L BA P+0.25 mg/L IAA+0.1 mg/L $GA_3$+30 g/L sucrose+0.8% agar, pH 5.8;

Co-culture medium (M C): GBA+acetosyringone (A CS) (100 mol/L)+30 g/L sucrose+0.8% agar, pH 5.8;

Screening culture medium (M B): GBA+Carb 400 mg/L+ hygromycin 10 mg/L+30 g/L sucrose+0.8% agar, pH 5.8;

Rooting medium (M R): ½M $S_0$+0.2 mg/L N A A+250 mg/L Carb+5 mg/L hygromycin+30 g/L sucrose+0.8% agar, pH 5.8.

4. Preparation of Explants

The seeds that were filled, uniform in size and had no pests and diseases were selected, decorticated, soaked with 70% ethanol for 1 min, rinsed with sterilized water twice, sterilized with 1% $AgNO_3$ for 3 min, and rinsed with sterilized water for three times. The seeds were sowed onto a $MS_0$ solid culture medium and sprouted in dark at 28° C.; sterile seedlings were obtained after culture for 36-48 h. Roots, cotyledons and phyllopodiums of sterile seedlings were cut to reveal stem tips, and then cut longitudinally. The obtained explants contained a half of stem tip meristems and two halves of cotyledon axillary buds.

5. Infection

The prepared stem tip explants were soaked in bacterial solution sufficiently for 10 min, and then taken out. The sterile filter paper was used to absorb sufficiently the redundant bacterial solution on the surfaces of explants. The explants were placed onto a MC co-culture medium for co-culture of 3 d in dark at 28° C., and control was provided.

6. Transformant Screening and Plant Regeneration

The explants co-cultured for 3 d were transferred onto a screening culture medium MB containing 10 mg/mL hygromycin (Hyg) for culture of 2 weeks, and then screened for 2-3 turns (2 weeks for each turn). The selected resistant buds were transferred onto the rooting culture medium MR for induced rooting.

Genetic Transformation of *Taraxacum kok-saghyz* Rodin (Also Called Russian Dandelion)

1. Materials

*Taraxacum kok-saghyz* Rodin; *Agrobacterium* strain: GV3101; plasmid (pCAMBIA2300-35S-HF) which was a binary vector pCAMBIA2300 carrying the HF gene and resistant to Kanamycin.

2. Genetic Transformation and Regeneration of *Taraxacum kok-saghyz* Rodin (1) Tissue-cultured seedlings growing well were selected. The edges of the leaves were removed. The stem of *Taraxacum kok-saghyz* Rodin was cut into a length of 2 cm. The leaves were cut into the size of 1 $cm^2$. They were placed onto a MS culture medium added with plant hormones 6-BA and NAA for dark culture of 2 d;

(2) 200 µl was taken from *Agrobacterium* GV3101 glycerin tube stored at −70° C. and containing plasmid pCAMBIA2300-35S-HF to be inoculated into 50 ml of LB (50 mg/L Gen+100 mg/L Rif+50 mg/L Kan) liquid for culture overnight;

(3) The bacterial solution cultured overnight was streaked on the LB (50 mg/L Gen+100 mg/L Rif+50 mg/L Kan) solid culture medium, placed upside down, for culture of 2 d at 28° C.;

(4) Monoclonal colonies were selected for inoculation onto the LB (50 mg/L Gen+100 mg/L Rif+50 mg/L Kan) broth, for shaking culture of 2 d at 28° C.;

(5) The cultured bacterial solutions were respectively inoculated into 100 ml of LB (50 mg/L Gen+100 mg/L Rif+50 mg/L Kan) liquid at a ratio of 1:100 for enlarged culture, and activated till OD260 of about 0.6 for infection;

(6) The aforesaid two bacterial solutions were respectively placed into 2 50 ml sterile large centrifuge tubes, and centrifuged for 10 min at 5000 rpm;

(7) The supernatant was discarded. The bacteria was suspended by 100 ml of MS broth, and cultured for 5 min at 28° C.;

(8) The above explants cultured in dark for 2 d were placed into the selected bacterial solution for shaking culture of 20 min at 28° C.;

(9) The infected explants were spread on the sterile dry filter paper, with the redundant bacterial solution absorbed, for dark culture of 2 d;

(10) After 2 d, the explants were taken out and placed onto the MS (1 mg/L 6-BA+0.1 mg/L NAA+400 mg/L Cb (carbenicillin)+50 mg/L Kan (Kanamycin)) solid culture medium; the plate was poured every half a month;

(11) When adventitious shoots grew to 2 cm, single shoots were broken off and inserted into the rooting culture medium ½MS (0.2 mg/L NAA+50 mg/L Kan+400 mg/L Cb) for growing;

(12) After one month, the strong tissue-cultured seedlings were domesticated for 1 d, transplanted into nutrient soil (turfy soil:vermiculite=3:1), covered with film for 1 week, and placed in cultivation room for subsequent culturing.

Genetic Transformation of Maize

1. Materials and Reagents

Maize variety: Qi 319; *Agrobacterium* strain: GV3101; plasmid (pCAMBIA2300-35S-HF) which was a binary vector pCAMBIA2300 carrying the HF gene and resistant to Kanamycin.

D-culture medium: NaFeEDTA 10 ml/L+N6 macroelements 50 ml/L+B5 microelements 10 ml/L+Di comba (2,4-D) 1 ml/L (5 ml/L)+RTV 10 ml/L+Casamina acids (casein hydrolase) 0.5 g/L+L-Prine 700 mg/L+inositol 100 mg/L+ Sucrose 20 g/L, pH 5.8

D-Inf culture medium: NaFeEDTA 10 ml/L+N6 macroelements 50 ml/L+B5 microelements 10 ml/L+Di comba (2,4-D) 1 ml/L+RTV 10 ml/L+Casamina acids (casein hydrolase) 0.5 g/L+L-Prine 700 mg/L+inositol 100 mg/L+ Sucrose 68.5 g/L+glucose 36 g/L, pH 5.2

D-AS culture medium: D-culture medium+glucose 10 g/L+agar powder 8 g/L+AS (0.5 M) 200 μl+AgNO$_3$ 1 ml/L (both AS and AgNO$_3$ had the final concentration of 100 μM, and were added after sterilization of the culture medium when being slightly cool for uniform mixing)

D-Cef culture medium: D-culture medium+1 ml/L AgNO$_3$+cef 1 ml/L

2. Genetic Transformation and Regeneration of Maize (1) Preparation of maize immature embryo: maize leaves, maize silks and some redundant parts were peeled off; a knife was inserted into the upper portion for adding 70% ethanol; the maize entered the super-clean operating desk; 30 s later, it was taken out and blown dry on the super-clean operating desk for about 15-20 min; ⅔ of the surface of the grain was peeled off; immature embryo was peeled out.

(2) The bacterial solution added into D-Inf (containing AS) was diluted till OD600 of 0.3-0.5 and stood for more than 1 h. The immature embryo was washed once with D-Inf (free of AS), and then soaked into the bacterial solution, upside down with hand for 30 s, and stood for 5 min. Observed with no apparent wounds, the immature embryo was taken out, absorbed dry with sterile filter paper, and placed onto the D-AS solid culture medium for co-culture of 3 d in dark at 25° C.

(3) Stage of restoring culture: the immature embryo co-cultured for 3 d was rinsed in sterilized water (added with 1‰ of cef) for three times, 20 min for each time, and then absorbed dry with filter paper, and transferred onto the D-Cef solid culture medium, and restoring cultured in dark at 25° C. for 7 d. Thereafter, pressurization screening stage was performed: in 4 cycles, with the interval of 2 weeks between any two.

The 1$^{st}$ cycle: D culture medium+cef (1‰)+PPT (5 mg/ml)

The 2$^{nd}$ cycle: D culture medium+cef (1‰)+PPT (10 mg/ml)

The 3$^{rd}$ cycle: D culture medium+cef (1‰)+PPT (10 mg/ml)

The 4$^{th}$ cycle: D culture medium+cef (1‰)+PPT (10 mg/ml)

(4) Restoration stage after screening: D culture medium+6-BA (5 mg/L), wherein 2,4-D or Dicamba concentration was diluted by 5 times, and sucrose was 30 g/L (or sucrose 20 g/L, glucose 10 g/L); the period was 2 weeks; dark culture.

(5) Induction stage after screening: D culture medium+6-BA (5 mg/L), wherein 2,4-D or Dicamba concentration was diluted by 5 times, and sucrose was 50 g/L, without the addition of glucose, +cef 1 ml/L; dark culture.

(6) Differentiation stage: D culture medium, yet without the addition of any hormone; sucrose concentration was 30 mg/L, without the addition of glucose, +cef 1 ml/L; illumination culture.

(7) Rooting stage: ½ MS culture medium.

Genetic Transformation of False Flax (*Camelia saiva*) (by a Flower Dripping Method)

1. Materials and Reagents

*Camelina sativa*; *Agrobacterium* strain: GV3101; plasmid (pCAMBIA2300-35S-HF) which was a binary vector pCAMBIA2300 carrying the HF gene and resistant to Kanamycin.

2. Genetic Transformation of *Camelina sativa* by a Flower Dripping Method (1) Wild-type *Camelina sativa* was sowed in nutrient soil (humus:vermiculite:perlite=4:2:1), 5 grains/pot (diameter: 9 cm), and placed in cultivation room for culturing. The cultivation room had the temperature of 16 to 20° C. and the relative humidity of 60%. The illumination intensity was 4 000 1x. The illumination period was 16 h illumination/8 h dark. When the main stem of *Camelina sativa* plant grew to 5 cm and the lateral branches were just bud-like, the top inflorescences were removed to promote the growth and development of secondary branches. When the plants grew to the full-bloom stage, they were prepared for transformation. 2 d before transformation, the formed fruit pods were cut off.

(2) When *Agrobacterium* GV3101 containing the plasmid pCAMBIA2300-35S-HF was cultured till the OD600 value was 0.8, it was infiltrated isometrically into the culture medium (½ MS, 5% sucrose, 200 μL/L Silwet L-77) to re-suspend bacteria and transform *Camelina sativa*. Upon transformation, a pipettor was used to suck *Agrobacterium* re-suspension for infiltration into the culture medium and dripping onto the flower buds of *Camelina sativa*, ensuring that each flower bud was dripped. Thereafter, preservative films were used to coat the transformed plants to maintain humidity. The plants stood upright in dark in the cultivation room for culture of 1 d, and then were cultured under normal conditions.

(3) After the plants were mature, the seeds were collected and designated as TO generation seeds. 50 mg/L of kanamycin was used to screen the obtained TO generation *Camelina sativa* seeds to obtain positive transgenic plants.

The yield and biomass of the transgenic plants comprising the nucleic acid encoding the FTO obtained from the above methods and the control plants that do not comprise FTO were measured. The results are shown in table 2.

TABLE 2

Changes of the yield and biomass after the nucleic acid encoding the FTO were introduced into a variety of plants

| gene | Plant (Organs for evaluating the yield) | Yield Increased folds | Biomass (fresh weight of the overground parts after removing the seeds) Increased folds |
|---|---|---|---|
| Human FTO (SEQ ID NO: 5) | maize (seed) | 4.12 | 2.81 |
| | soybean (seed) | 4.00 | 2.75 |
| | tobacco (leaf) | 3.65 | 2.54 |
| | potato (tuber) | 3.83 | 2.61 |
| | alfalfa (stem and leaf) | 2.43 | 2.43 |
| | rape (seed) | 4.21 | 2.94 |
| | Russian dandelion (*Taraxacum kok-saghyz*) (rubber solution in the root) | 3.25 | 2.88 |
| | cotton (seed cotton) | 3.91 | 2.67 |
| | wheat | 3.78 | 2.58 |
| | millet (seed) | 4.08 | 2.79 |
| | flax (for oil) (seed) | 3.77 | 2.58 |
| | sunflower (seed) | 3.88 | 2.69 |
| | false flax (seed) | 4.09 | 2.79 |

From table 2, it can be seen that after FTO was introduced into a variety of plants, the yield and the biomass were increased.

The invention claimed is:

1. A matured maize or soybean plant expressing a protein having an amino acid sequence selected from SEQ ID NO: 1-4, wherein the plant has a yield of seeds at least four fold of that of the average yield of control plants grown under comparable conditions, wherein the control plants do not express the protein.

2. The plant of claim 1, wherein the plant is maize.

3. The plant of claim 1, wherein the plant is soybean.

4. The plant of claim 1, wherein the plant is a matured maize plant expressing a protein having the amino acid sequence of SEQ ID NO: 1.

5. The plant of claim 1, wherein plant is a matured soybean plant expressing a protein having the amino acid sequence of SEQ ID NO: 1.

6. A preparation of seeds obtained from a plurality of mature plants engineered to express a protein having a sequence selected from SEQ ID NO: 1-4, wherein the seeds comprise a protein having a sequence selected from SEQ ID NO: 1-4 or a nucleic acid encoding a protein having a sequence selected from SEQ ID NO: 1-4; and wherein the preparation of seeds has at least four fold more weight than that from a comparable plurality of the plants not so engineered, and wherein the plants are maize plants, or are soybean plants.

7. The preparation of seeds of claim 6, wherein the mature plants are mature maize plants.

8. The preparation of seeds of claim 6, wherein the mature plants are mature soybean plants.

9. The preparation of seeds of claim 6, wherein the mature plants are mature maize plants engineered to express a protein having the sequence of SEQ ID NO: 1.

10. The preparation of seeds of claim 6, wherein the mature plants are mature soybean plants engineered to express a protein having the sequence of SEQ ID NO: 1.

* * * * *